United States Patent
Sullivan

(10) Patent No.: US 12,377,279 B2
(45) Date of Patent: *Aug. 5, 2025

(54) WEARABLE CARDIOVERTER DEFIBRILLATOR (WCD) SYSTEM DETECTING QRS COMPLEXES IN ECG SIGNAL BY MATCHED DIFFERENCE FILTER

(71) Applicant: West Affum Holdings DAC, Dublin (IE)

(72) Inventor: Joseph L. Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/390,583

(22) Filed: Dec. 20, 2023

(65) Prior Publication Data

US 2024/0131349 A1    Apr. 25, 2024

Related U.S. Application Data

(63) Continuation of application No. 17/392,611, filed on Aug. 3, 2021, now Pat. No. 11,850,438, which is a continuation of application No. 15/724,317, filed on Oct. 4, 2017, now Pat. No. 11,077,310.

(60) Provisional application No. 62/404,140, filed on Oct. 4, 2016.

(51) Int. Cl.
*A61N 1/00* (2006.01)
*A61B 5/366* (2021.01)
*A61N 1/39* (2006.01)

(52) U.S. Cl.
CPC ............ *A61N 1/3987* (2013.01); *A61B 5/366* (2021.01); *A61N 1/3904* (2017.08); *A61N 1/3925* (2013.01)

(58) Field of Classification Search
CPC ...... A61N 1/3987; A61N 1/39; A61N 1/3904; A61N 1/3925; A61B 5/72–7292; A61B 5/024–0255; A61B 5/349–366
See application file for complete search history.

(56) References Cited

U.S. PATENT DOCUMENTS

| | | | |
|---|---|---|---|
| 3,724,455 A | 4/1973 | Unger | |
| 4,240,442 A | 12/1980 | Andresen et al. | |
| 4,583,524 A | 4/1986 | Hutchins | |
| 4,619,265 A | 10/1986 | Morgan et al. | |

(Continued)

FOREIGN PATENT DOCUMENTS

WO    9839061 A2    9/1998

OTHER PUBLICATIONS

Duncker et al. "Real-world Experience of 355 Consecutive Patients with a Wearable Cardioverter/Debrillator—Single Centre Analysis" Europace 2017, No. 19 Supplemental 3, iii304.

(Continued)

*Primary Examiner* — Scott M. Getzow
(74) *Attorney, Agent, or Firm* — POLSINELLI PC

(57) ABSTRACT

In embodiments, a wearable cardioverter defibrillator (WCD) system includes electrodes that render an ECG signal of the patient, and a processor that receives ECG data are derived from the rendered ECG signal. The processor may filter the received ECG data with a matched difference filter to detect QRS complexes, and compute a heart rate from the detected QRS complexes. The matched difference filter itself can have coefficient values associated with a baseline QRS complex, which improves detection.

20 Claims, 19 Drawing Sheets

SAMPLE COMPONENTS OF WEARABLE CARDIOVERTER DEFIBRILLATOR (WCD) SYSTEM

(56) References Cited

U.S. PATENT DOCUMENTS

| | | |
|---|---|---|
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,271,411 A | 12/1993 | Ripley et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,024,037 B2 | 9/2011 | Kumar |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 9,757,581 B2 | 9/2017 | Sullivan et al. |
| 10,322,291 B2 | 6/2019 | Medema et al. |
| 2003/0158593 A1 | 8/2003 | Heilman et al. |
| 2004/0230105 A1 | 11/2004 | Geva et al. |
| 2005/0107833 A1 | 5/2005 | Freeman et al. |
| 2005/0107834 A1 | 5/2005 | Freeman et al. |
| 2008/0027338 A1 | 1/2008 | Lu et al. |
| 2008/0312709 A1 | 12/2008 | Volpe et al. |
| 2009/0005827 A1 | 1/2009 | Weintraub et al. |
| 2010/0007413 A1 | 1/2010 | Herleikson et al. |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0150008 A1 | 1/2012 | Lanar et al. |
| 2012/0112903 A1 | 5/2012 | Kaib et al. |
| 2012/0144551 A1 | 6/2012 | Guldalian |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0265845 A1 | 9/2015 | Sullivan et al. |
| 2015/0328472 A1 | 11/2015 | Sullivan et al. |
| 2016/0004831 A1 | 1/2016 | Carlson et al. |
| 2016/0007877 A1 | 1/2016 | Felix et al. |
| 2016/0082277 A1 | 3/2016 | Foshee, Jr. et al. |
| 2016/0278659 A1 | 9/2016 | Kaib et al. |
| 2017/0056682 A1 | 3/2017 | Kumar et al. |
| 2018/0093102 A1 | 4/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0221648 A1 | 8/2018 | Gustavson et al. |
| 2018/0318593 A1 | 11/2018 | Sullivan |
| 2019/0030351 A1 | 1/2019 | Sullivan et al. |
| 2019/0030352 A1 | 1/2019 | Sullivan et al. |

OTHER PUBLICATIONS

Heartstart MRx and XL AED Algorithm—Application Note, Jul. 2001, Edition 2 Philips Healthcare, USA.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi: 10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Olgin JE, Pletcher MJ, Vittinghoff E, et al., "Wearable Cardioverter-Defibrillator after Myocardial Infarction," N Engl J Med Sep. 27, 2018; 379(13):1205-1215.

Pagan-Carlo, et al., "Encircling Overlapping Multipulse Shock Waveforms for Transthoracic Defibrillation," JACC Journals, Dec. 1998, vol. 32 Issue 7, pp. 2065-2071.

Schuhmann et al., "Experience with the wearable cardioverter defibrillator (WCD) in high risk cardiac patients from a German single center cohort", Heart Rhythm 2016;13(5):S254.

WCD Performance for Clinical Review, Sullivan et al., "A Novel Wearable Cardioverter Defibrillator With Reduced False Alarm Rate," AHA 2017.

Zoll, LifeVest, Proven protection from Sudden Cardiac Death, issued Mar. 27, 2018, 4 pages. Pittsburgh PA, USA.

SAMPLE COMPONENTS OF WEARABLE CARDIOVERTER DEFIBRILLATOR (WCD) SYSTEM

SAMPLE COMPONENTS OF EXTERNAL DEFIBRILLATOR

SAMPLE RENDERED ECG SIGNAL

*TAKING TIME DERIVATIVE OF ECG SIGNAL*

700

$$\text{Output}(n) = \sum_{m=0}^{length(f)} f(m) * g(m-n)$$

COMPUTATION FOR MATCHED FILTER
(CONVOLUTION)

KERNEL OF
SAMPLE MATCHED FILTER

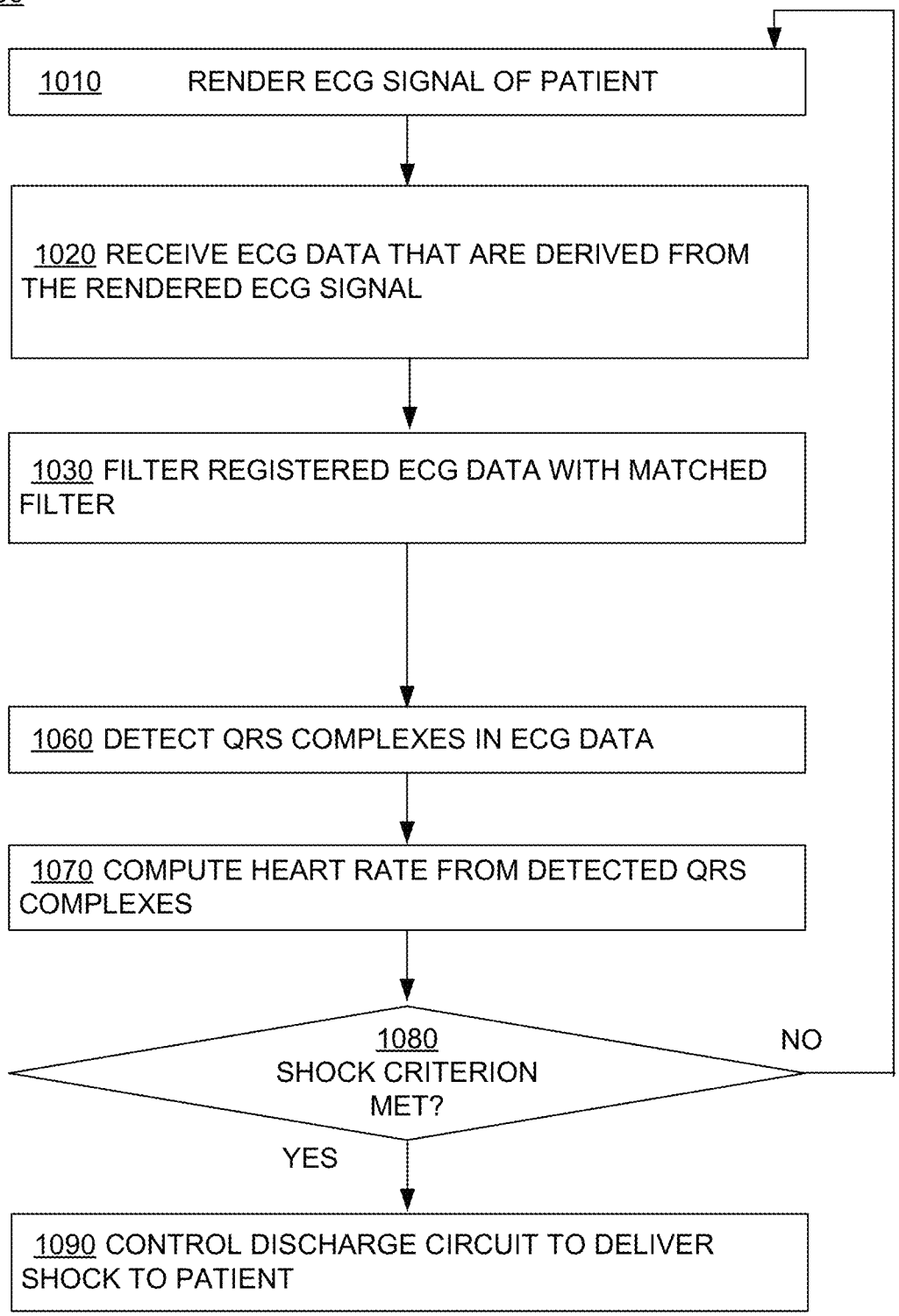
FIG. 10 — METHODS

1100A $$\text{Output}(n) = 1 - \text{MDT}\{n, F[f(m)]\text{-}G[g(m)]\}$$

FIG. 11A

1100B $$\text{Output}(n) = 1 - \frac{\sum_{m=0}^{length(f)}(f(m)-g(m-n))^2}{\sum_{m=0}^{length(f)}(f(m)^2+g(m)^2)}$$

FIG. 11B

*COMPUTATIONS FOR
MATCHED DIFFERENCE FILTER*

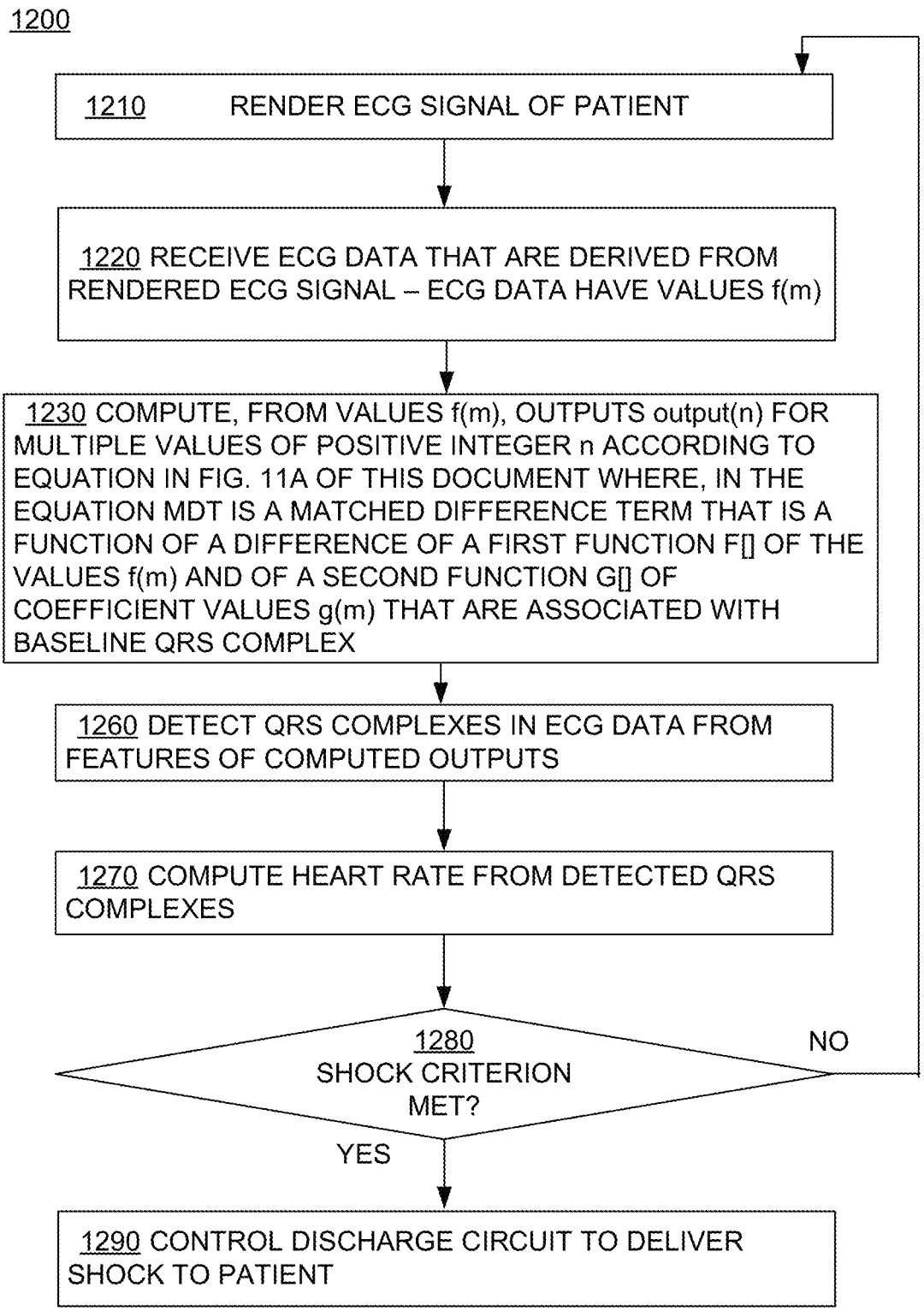
FIG. 12    *METHODS*

FIG. 15    METHODS

1660

1700

1800

FIG. 17 METHODS

FIG. 18  METHODS

PEAK DETECTION

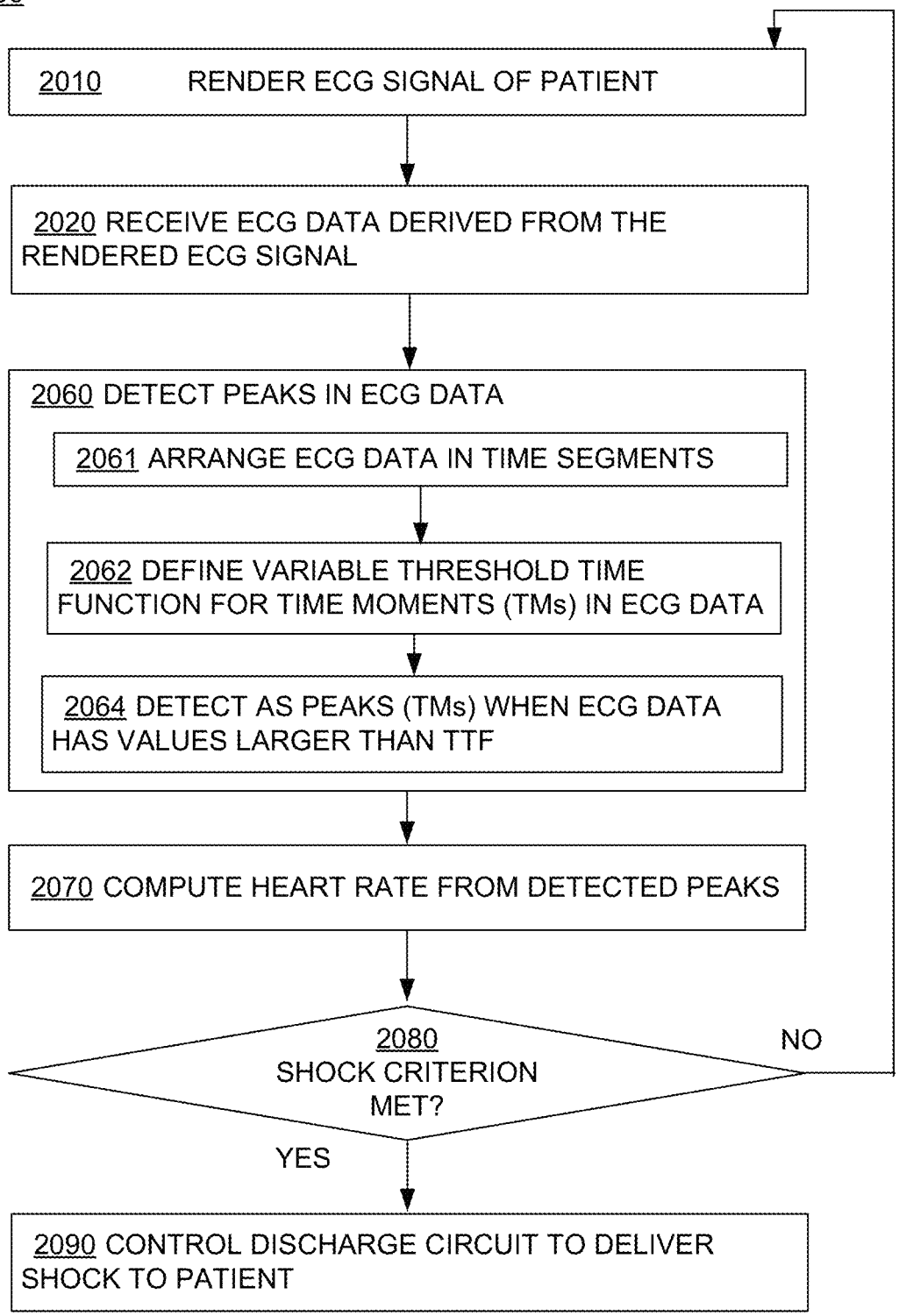
FIG. 20  *METHODS*

*PEAKS SELECTION PER POLARITY*

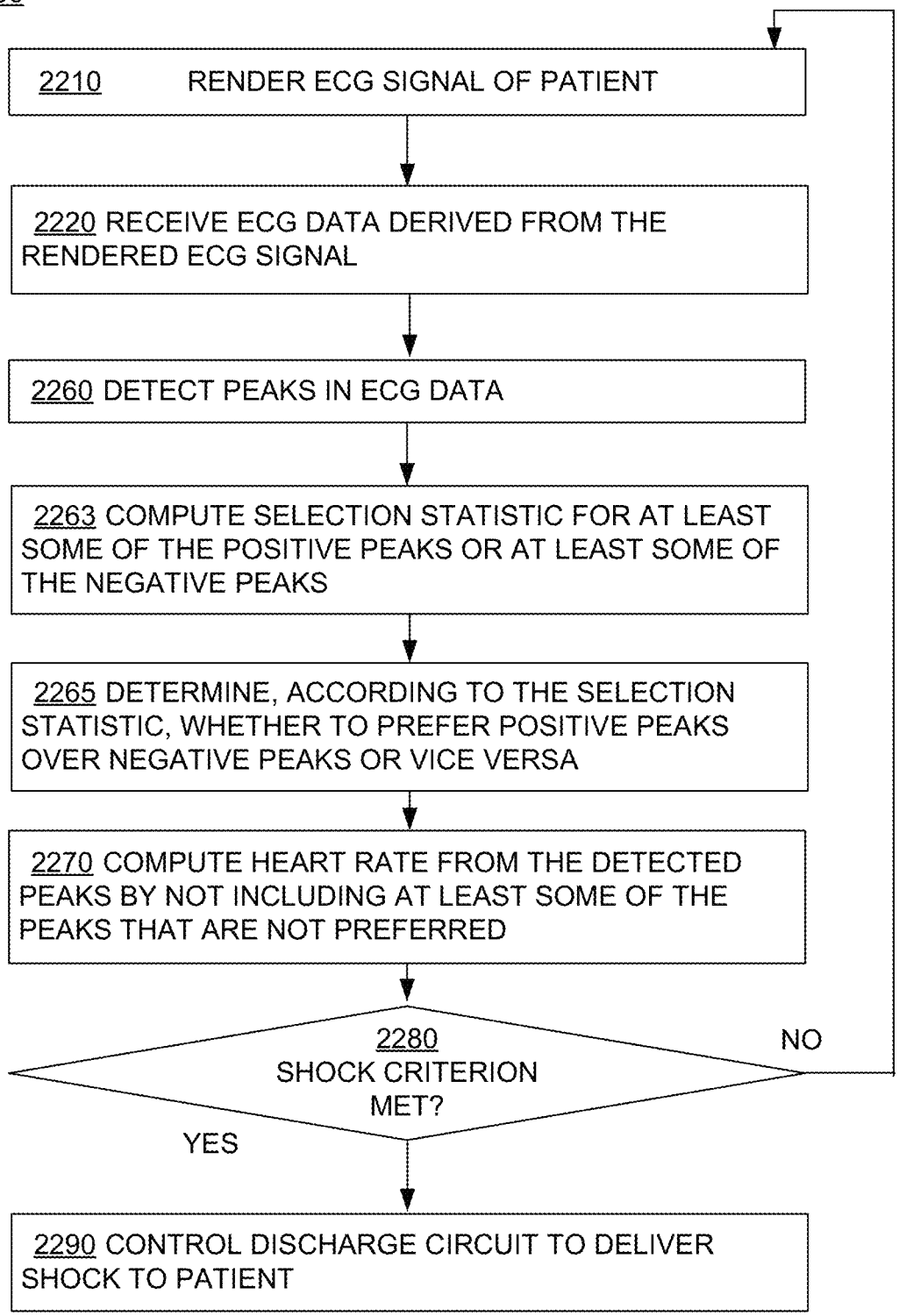
FIG. 22  METHODS

WEARABLE CARDIOVERTER DEFIBRILLATOR (WCD) SYSTEM DETECTING QRS COMPLEXES IN ECG SIGNAL BY MATCHED DIFFERENCE FILTER

CROSS REFERENCE TO RELATED PATENT APPLICATIONS

The present application is a continuation of U.S. application Ser. No. 17/392,611 filed Aug. 3, 2021 (pending) which is a continuation of U.S. application Ser. No. 15/724,317 filed Oct. 4, 2017, now U.S. Pat. No. 11,077,310. Said application Ser. No. 15/724,317 claims the benefit of U.S. Provisional Patent Application No. 62/404,140, filed on Oct. 4, 2016, the disclosure of which is hereby incorporated by reference. Said application Ser. No. 17/392,611, said application Ser. No. 15/724,317, and said Application No. 62/404,140 are hereby incorporated herein in their entireties.

BACKGROUND

All subject matter discussed in this Background section is not necessarily prior art, and may not be presumed to be prior art simply because is presented in this Background section. Along these lines, any recognition of problems in the prior art discussed in this Background section or associated with such subject matter should not be treated as prior art unless expressly stated to be prior art. Rather, the discussion of any subject matter in this Background section should be treated as part of the inventor's approach to the particular problem, which in and of itself may also be inventive.

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

Sometimes a WCD system fails to make a consistently good electrical contact with the patient's skin. Indeed, the wearable components may shift with respect to the skin, which creates artifacts in the ECG that is being detected. Another name for these artifacts is electrical noise. These artifacts may be larger in magnitude than the ECG that the WCD system is trying to detect and monitor, which make detection more challenging.

BRIEF SUMMARY

The present description gives instances of wearable cardioverter defibrillator (WCD) systems, storage media that store programs, and methods, the use of which may help overcome problems and limitations of the prior art.

In embodiments, a wearable cardioverter defibrillator (WCD) system includes electrodes that render an ECG signal of the patient, and a processor that receives ECG data are derived from the rendered ECG signal. The processor may filter the received ECG data with a matched filter to detect QRS complexes, and compute a heart rate from the detected QRS complexes. The matched filter itself can have coefficient values associated with a baseline QRS complex, which improves detection.

In embodiments, a wearable cardioverter defibrillator (WCD) system includes electrodes that render an ECG signal of the patient, and a processor that receives ECG data are derived from the rendered ECG signal. The processor may filter the received ECG data with a matched difference filter to detect QRS complexes, and compute a heart rate from the detected QRS complexes. The matched difference filter itself can have coefficient values associated with a baseline QRS complex, which improves detection.

In embodiments, a wearable cardioverter defibrillator (WCD) system includes electrodes that render an ECG signal of the patient, and a processor that receives ECG data are derived from the rendered ECG signal. The processor may search for peaks in the ECG signal forward and backward with threshold functions. The dual search direction may improve rejection of noise that might be detected as peaks. The processor may then compute a heart rate that more accurately.

In embodiments, a wearable cardioverter defibrillator (WCD) system includes electrodes that render an ECG signal of the patient, and a processor that receives ECG data are derived from the rendered ECG signal. The processor may detect peaks in the ECG signal according to a variable threshold, which may adjust for local amplitude variations of the ECG signal. The processor may then compute a heart rate that more accurately.

In embodiments, a wearable cardioverter defibrillator (WCD) system includes electrodes that render an ECG signal of the patient, and a processor that receives ECG data are derived from the rendered ECG signal. Upon searching for peaks in the ECG signal, the processor may detect peaks of both polarities, positive and negative. The processor may then compute a selection statistic for determining which one of the polarities is preferred over the other. The processor may then compute a heart rate by rejecting peaks of the polarity that is not the preferred one. The heart rate computation may thus be more accurate.

These and other features and advantages of the claimed invention will become more readily apparent in view of the embodiments described and illustrated in the present disclosure, namely from the present written specification and the drawings.

BRIEF DESCRIPTION OF THE DRAWINGS

FIG. 10 is a flowchart for illustrating methods according to embodiments.

FIG. 11A shows a sample equation for computing outputs for a filter, such as the filter of FIG. 6, in embodiments where the filter is a matched difference filter.

FIG. 11B shows a particular sample equation that is a special case of equation of FIG. 11A, according to embodiments.

FIG. 12 is a flowchart for illustrating methods according to embodiments.

FIG. 20 is a flowchart for illustrating methods according to embodiments.

FIG. 22 is a flowchart for illustrating methods according to embodiments.

DETAILED DESCRIPTION

As has been mentioned, the present description is about wearable cardioverter defibrillator (WCD) systems, storage media that store programs, and methods. Embodiments are now described in more detail.

A wearable cardioverter defibrillator (WCD) system made according to embodiments has a number of components. These components can be provided separately as modules that can be interconnected, or can be combined with other components, etc.

Figure 1:
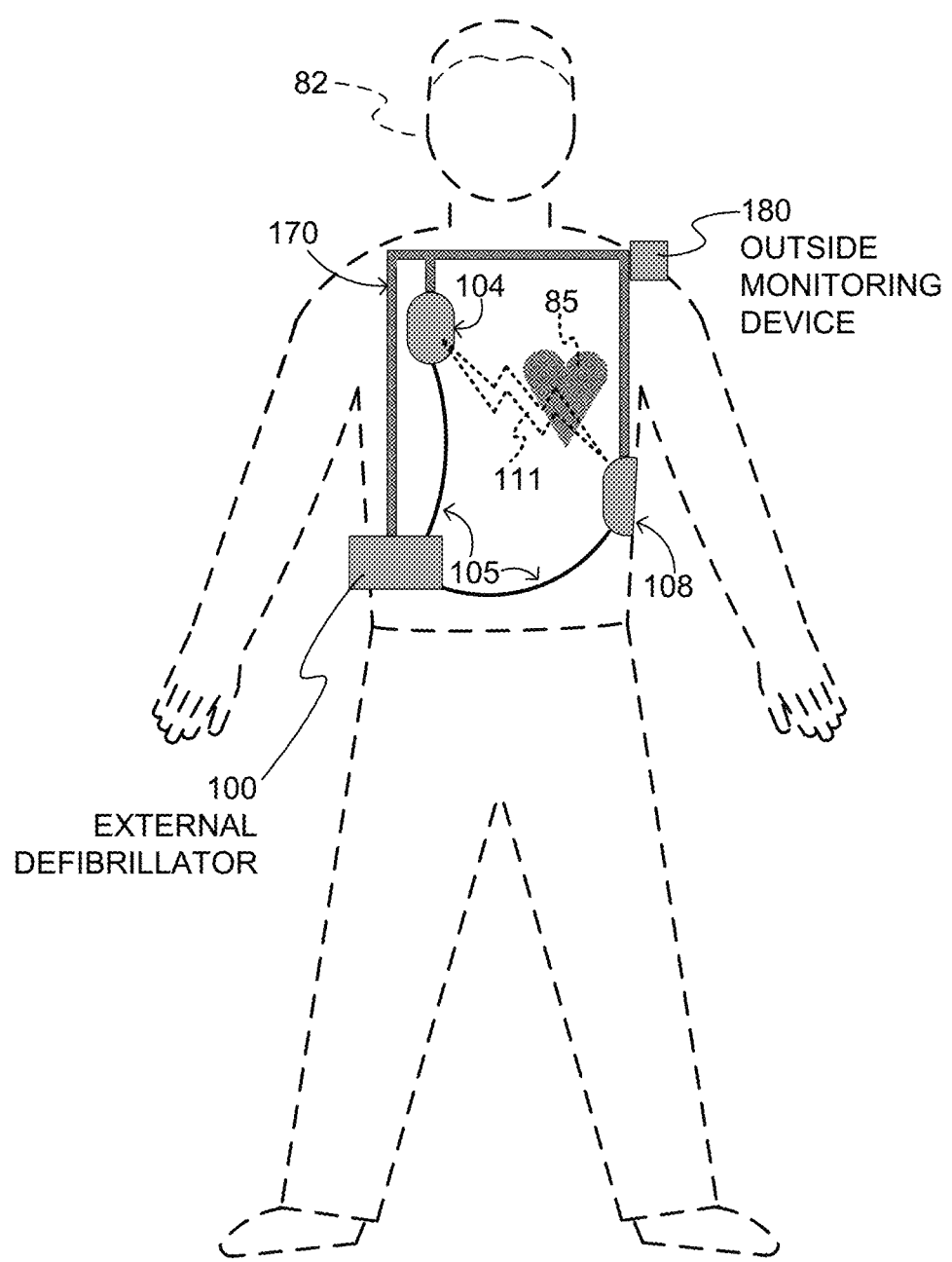
FIG. 1 is a diagram of components of a sample wearable cardioverter defibrillator (WCD) system, made according to embodiments.

FIG. 1 depicts a patient 82. Patient 82 may also be referred to as a person and/or wearer, since that patient wears components of the WCD system. Patient 82 is ambulatory, which means patient 82 can walk around and is not bedridden.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US 2017/0056682 A1, which is incorporated herein by reference. Of course, in such embodiments, the person skilled in the art will recognize that additional components of the WCD system can be in the housing of a support structure instead of attached externally to the support structure, for example as described in the 2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as shock, defibrillation shock, therapy or therapy shock, is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data are obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
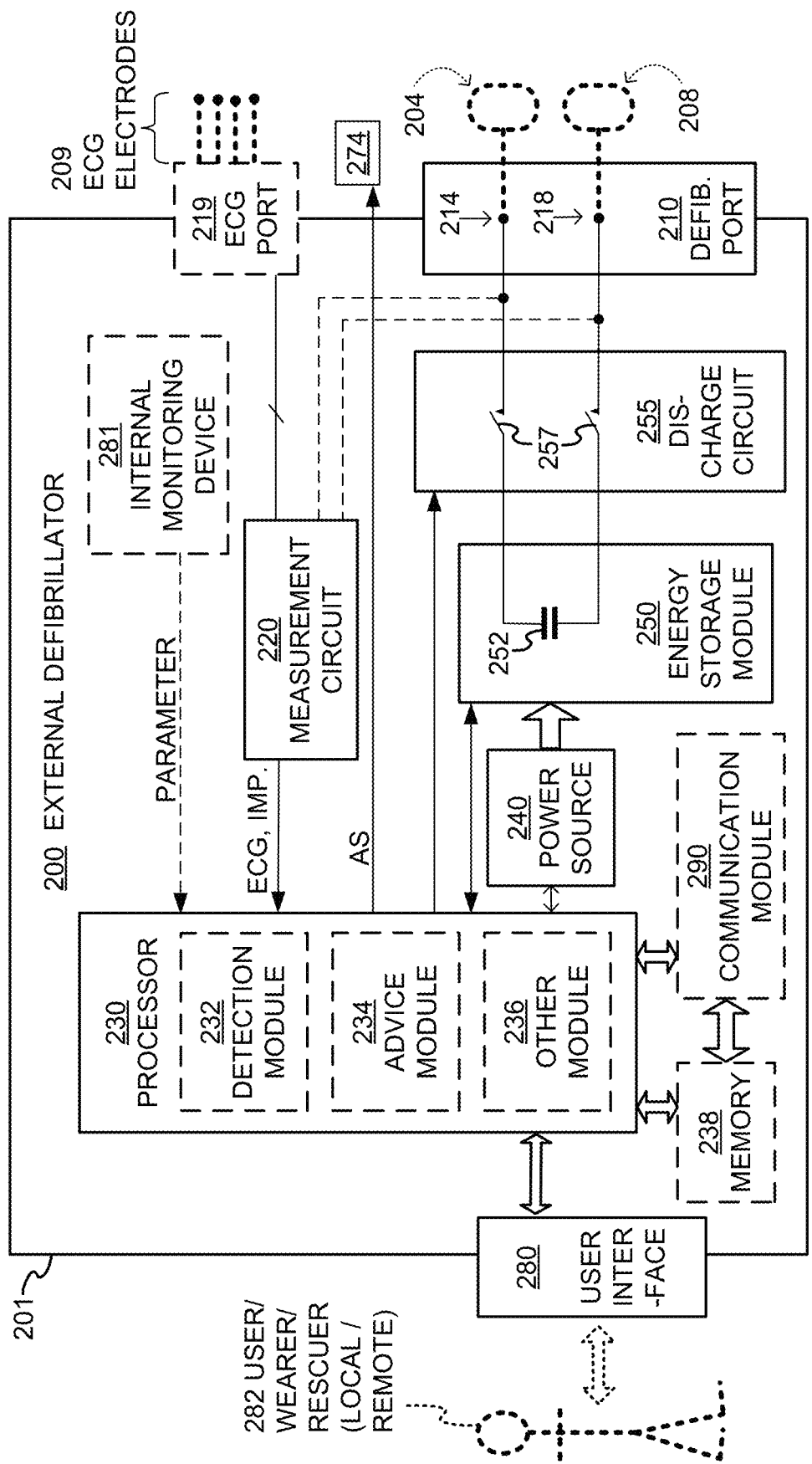
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which monitoring device can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body.

Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, one of the transducers may include a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a WCD system according to embodiments also includes a fluid that it can deploy automatically between the electrodes and the patient's skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from processor 230 that is described more fully later in this document.

In some embodiments, defibrillator 200 also includes a measurement circuit 220, as one or more of its sensors or transducers. Measurement circuit 220 senses one or more electrical physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. Module 290 may also include such sub-components as may be deemed necessary by a person skilled in the art, for example an antenna, portions of a processor, supporting electronics, outlet for a telephone or a network cable, etc. This way, data, commands, etc. can be communicated. The data can include patient data, event information, therapy attempted, CPR performance, system data, environmental data, and so on.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

As mentioned above, electrodes 209, or even electrodes 204 & 208 can be configured to render an electrocardiogram (ECG) signal of the patient, while the patient is wearing the support structure. An instance is now described.

Figure 3:
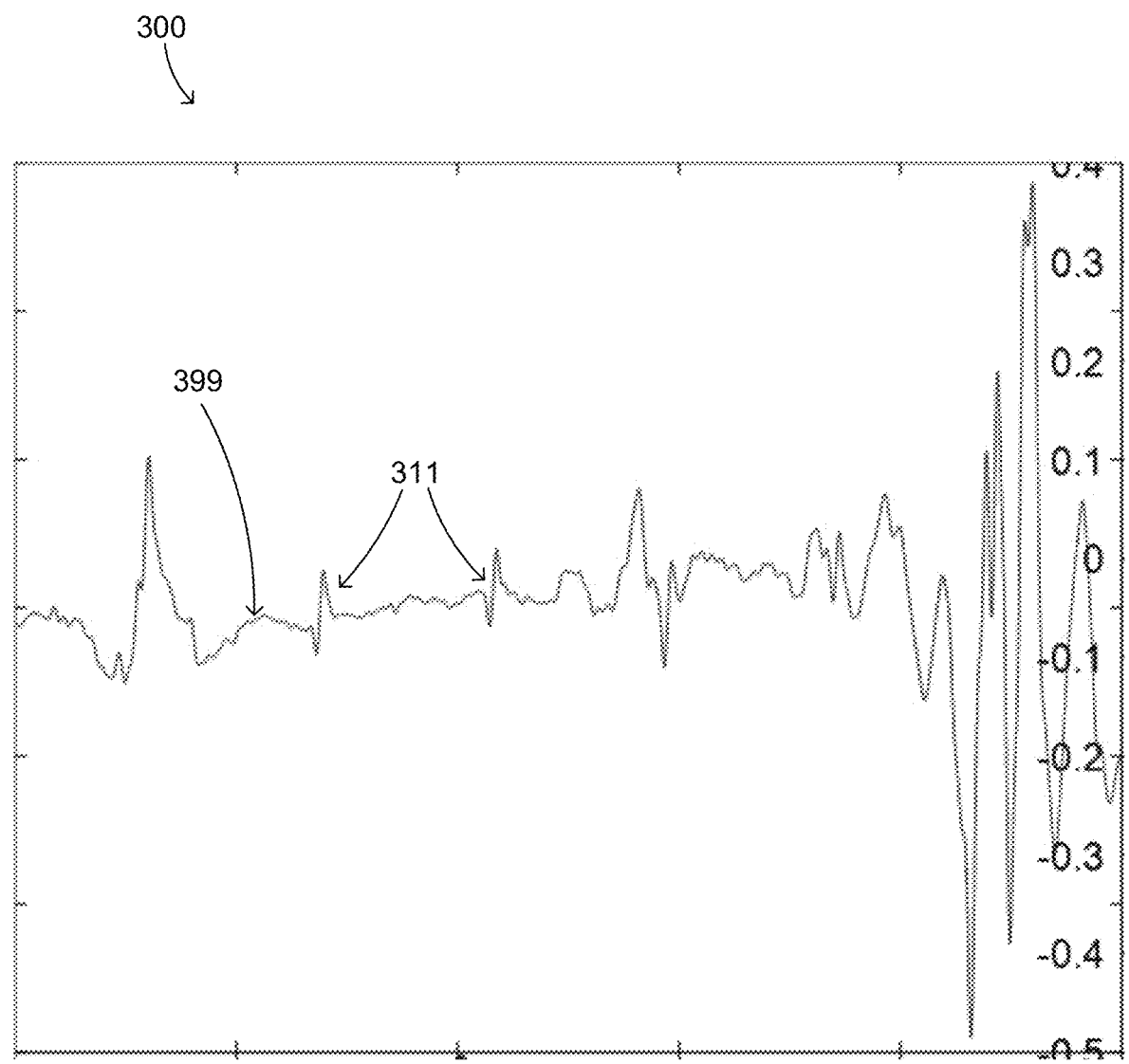
FIG. 3 is a time diagram of a sample ECG signal rendered by embodiments.

FIG. 3 is a time diagram 300 showing a sample ECG signal 399 rendered by embodiments. This depiction could be arrived at, for example, by sampling the actual analog ECG signal from the electrodes, to arrive at digital ECG data that have digital values f(m). Accordingly, this description may use the terms signal, data and values interchangeably.

It will be desirable for processor 230 to determine the activity of heart 85, at least from ECG signal 399. In particular, it is often desired to detect QRS complexes, or at least local peaks in ECG signal 399, which somehow signify the activity of the heart. These QRS complexes, or at least peaks, may be used at least for computing the patient's heart rate.

Looking at ECG signal 399, to the trained human eye features 311 appear to be QRS complexes, of the type that are being sought to be detected. Of course, these seeming QRS complexes do not look like standard QRS complexes, but are instead somewhat distorted by electrical noise that does not seem excessive in their region. There could be additional QRS complexes in ECG signal 399, which are wholly obscured by excessive noise.

Further as mentioned above, processor 230 can be configured to receive ECG data that are derived from the rendered ECG signal. The process may involve filtering. The process may or may not involve also taking a first time derivative of the ECG signal, or of the data that represents it, and so on. Examples are now described.

Figure 4:
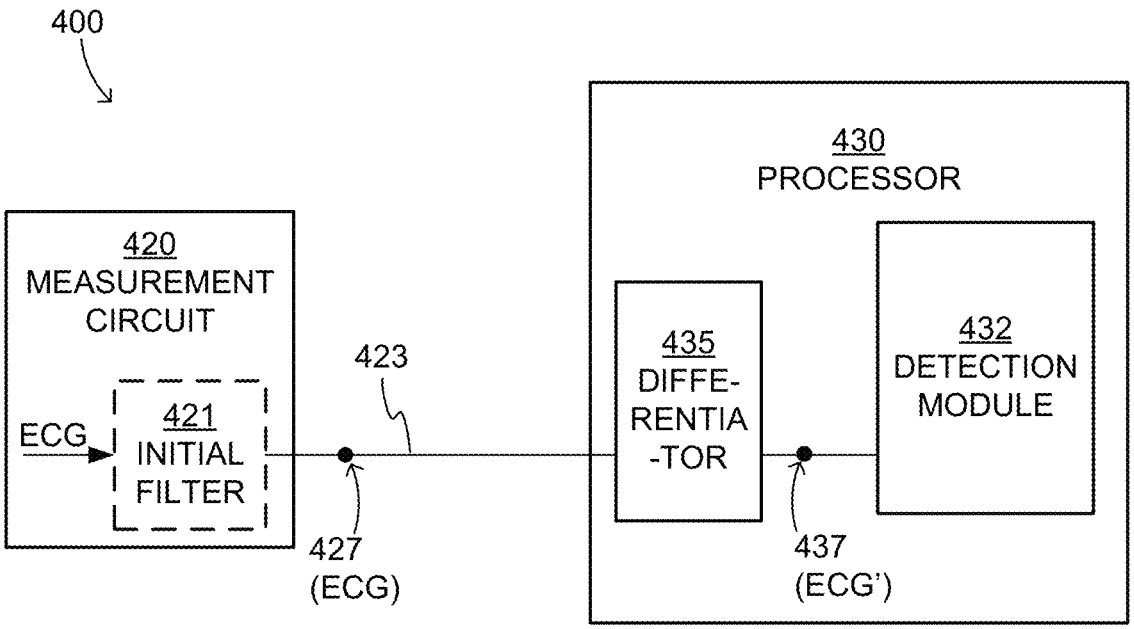
FIG. 4 is a block diagram of sample embodiments that take a time derivative of an ECG signal.

FIG. 4 is a block diagram of sample embodiments 400 that take a time derivative of an ECG signal. Embodiments 400 include a measurement circuit 420 and a processor 430, which could be used for implementing measurement circuit 220 and a processor 230 respectively. Measurement circuit 420 can be coupled with processor 430 by at least one conductor 423, whose one sample node 427 is indicated.

Measurement circuit 420 renders the ECG signal internally, whether in analog or digital form. Measurement circuit 420 may include an optional initial filter 421. If provided, initial filter 421 may perform one or more types of filtering to the rendered ECG signal, such as passband filtering between 2.75 Hz-25 Hz to remove artifacts at different frequencies, etc. In digital embodiments, initial filter 421 can be implemented by a conventional Finite Impulse Response (FIR) filter. In other embodiments, initial filter 421 can be provided within processor 430, operating digitally. As such, at point 427 the signal or values are those of the ECG signal, possibly filtered.

Processor 430 includes a detection module 432, which can be a way to implement detection module 232. Processor 430 may also include a differentiator 435 that is coupled to receive the ECG signal or values from conductor 423. Processor 430 can be further configured, via differentiator 435, to take a time derivative of the received ECG data, before detection module 432 performs its other computations for detecting a QRS complex or peaks. For example, if the signal is data values, differentiator 435 can be computing difference values between successive data values. As such, from a node 437, detection module 432 receives and registers data ECG' that have values representing a time derivative of the rendered ECG signal.

Figure 5:
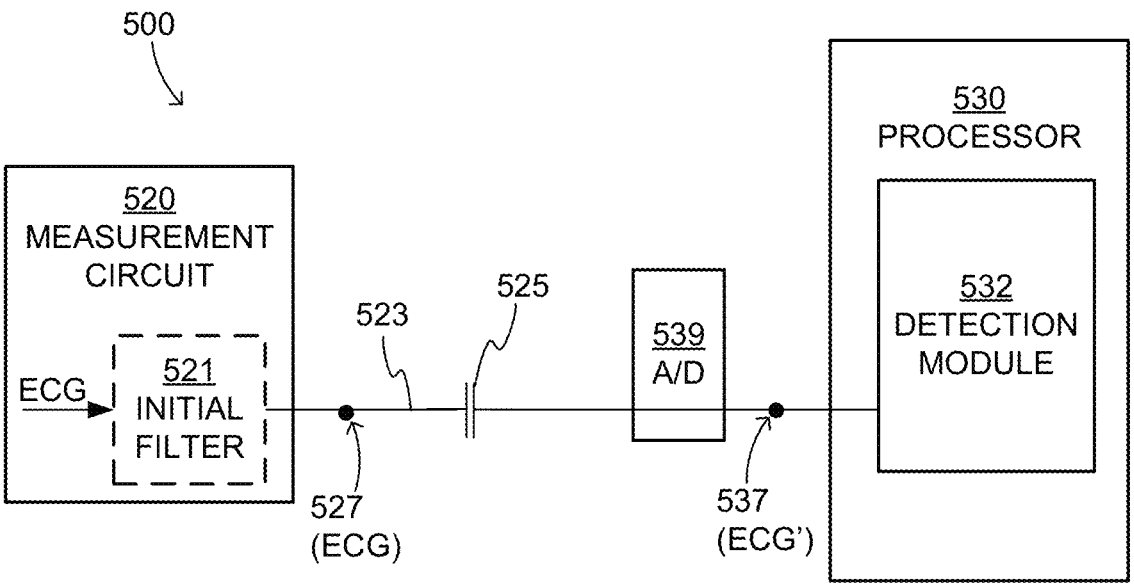
FIG. 5 is a block diagram of other sample embodiments that take a time derivative of an ECG signal.

FIG. 5 is a block diagram of other sample embodiments 400 that take a time derivative of an ECG signal. Embodiments 500 include a measurement circuit 520 and a processor 530, which could be used for implementing measurement circuit 220 and a processor 230 respectively.

Measurement circuit 520 can be coupled with processor 530 by at least one conductor 523, whose one sample node 527 is indicated. A capacitor 525 is coupled in series with respect to conductor 523, between measurement circuit 520 and a processor 530. An Analog to Digital (A/D) converter 539 may also be provided as shown. Capacitor 525 and A/D converter 539 may alternately be provided as part of measurement circuit 520.

Measurement circuit 520 may render the ECG signal internally in analog form. Measurement circuit 520 may include an optional initial filter 521, which can be analog, for the same types of functions as filter 421. As such, the analog ECG signal, possibly filtered, is at point 527.

At node 537, the ECG signal of the patient has been passed through capacitor 525 in series, and through A/D converter 539. Processor 530 includes a detection module 532, which can be a way to implement detection module 232. As such, from a node 537, detection module 532 of processor 530 receives and registers data ECG' that have values representing a time derivative of the rendered ECG signal.

Figure 6:
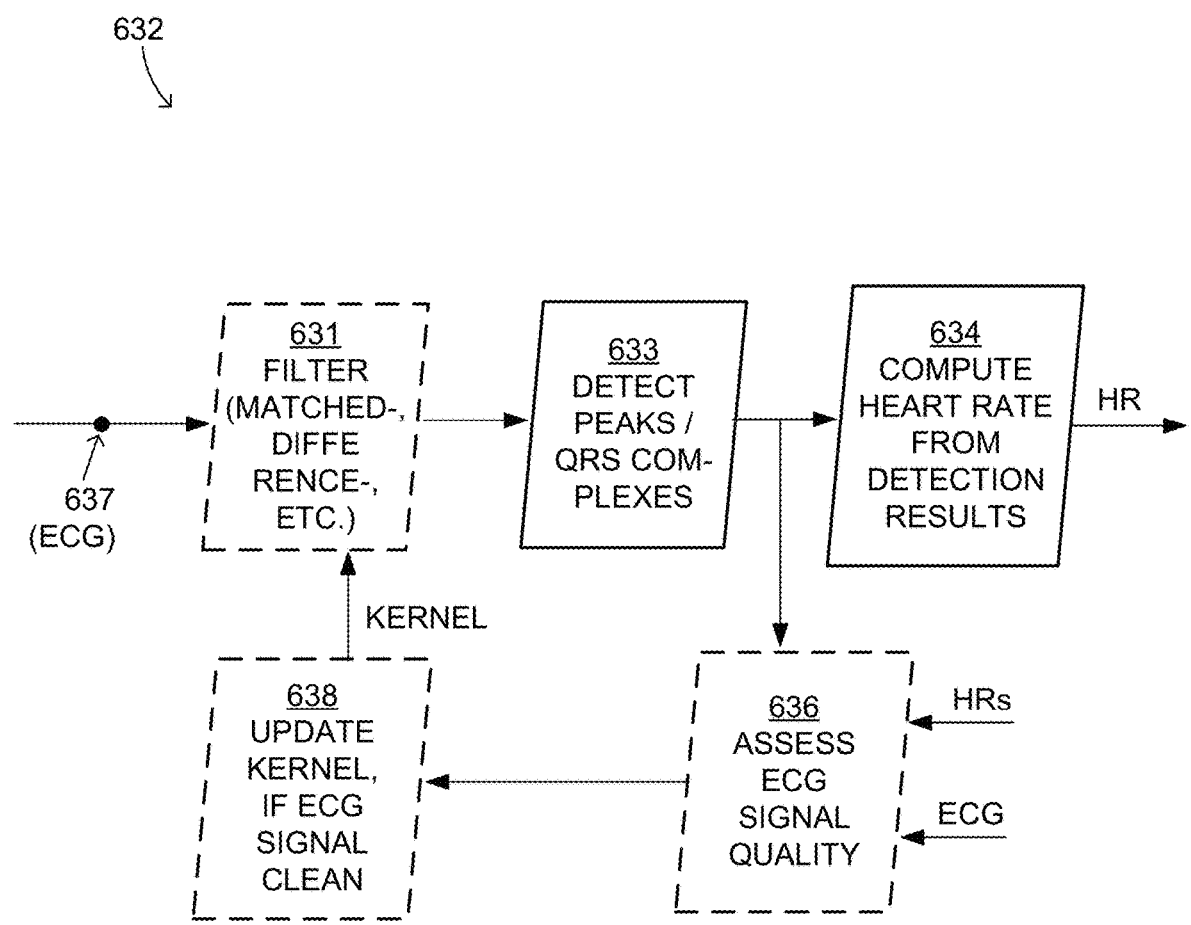
FIG. 6 is an action diagram of QRS detection processes for computing the patient's heart rate, according to embodiments.

FIG. 6 is an action diagram 632 of QRS detection processes according to embodiments, for computing the patient's heart rate. Action diagram 632 is technically a flowchart, because each block nominally stands for actions. Action diagram 632 is given this way to indicate the arrangement of computing blocks that would perform the corresponding actions.

Data from the rendered ECG signal are provided on node 637. This data can be as described above, also for nodes 437 and 537. ECG data may be processed in time segments. The data of a segment can be stored in memory 238, and then be processed as a batch. Batch processing may help with techniques such as using the matched filter, processing the signal forward and backward, or making multiple passes through the data before deciding on the QRS complexes.

According to an optional action block 631, the data at node 637 can be passed through a filter. The filter can be a matched filter, a matched difference filter, a comparator for high values, and so on. Examples for some are provided later in this document. In case of a matched filter or a matched difference filter each segment of data can be processed with a previously-established kernel.

According to an action block 633, peaks and/or QRS complexes may be detected from outputs of the filtering of action block 631. According to an action block 634, a heart rate (HR) is computed from the detection results of action block 633.

A feedback loop may update the kernel that is being used. In general, the ECG signal quality can be assessed. If the signal is clean, then the kernel is updated for the next segment.

In particular, an action block 636 may receive the detection results of action block 633. Action block 636 may also receive heart rates detected from other channels, and/or the ECG signal itself. Action block 636 may thus assess signal quality. Signal quality can be assessed using a number of metrics, for example:

a) Heart rate agreement. If multiple channels give similar heart rates, then they are given a high "agreement" value.

b) QRS organization. If QRS complexes in a single segment have a similar morphology then that channel is given a high "organization" value. Slightly less organization is required for channels with very high agreement values.

The feedback loop can close with an action block 638 that updates the kernel of action block 631. The filter kernel can be updated for channels with a high heart rate agreement and a high QRS organization. If multiple channels are used, a different kernel may be stored for each, as QRS morphology varies from one channel to the next, and may very over time. Since the device is worn 24 hours/day, there is plenty of opportunity to look for a clean signal to update the kernel.

Figures 7, 8:
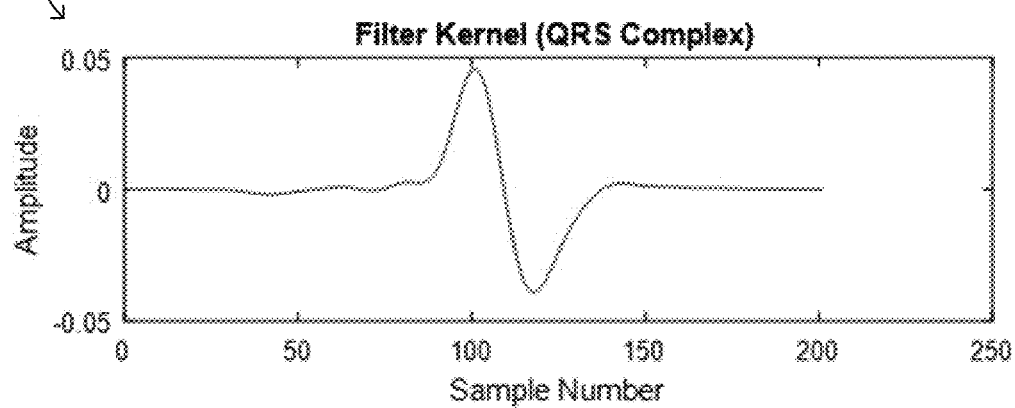
FIG. 7 shows a sample equation for computing outputs for a filter, such as the filter of FIG. 6, in embodiments where the filter is a matched filter.
FIG. 8 is a diagram of coefficient values for a kernel of a matched filter for detecting a QRS complex of a sample patient made according to embodiments.

FIG. 7 shows a sample equation 700 for computing outputs for a filter. For example, equation 700 can be used by action block 631 when the filter is a matched filter. Equation 700 is similar to one for convolution, and in particular discrete convolution. The convolution of two finite sequences is defined by extending the sequences to finitely supported functions on the set of integers. In equation 700, f(m) are the data values of the ECG signal, which can be as in FIG. 3. While equation 700 is similar to convolution however, it is not identical to it. Indeed, while convolution uses the indexes g(n-m), a matched filter uses them in reverse order, which is also time order g(m-n). Moreover, for the matched filter in equation 700, g( ) are the coefficient values that define the kernel, and are chosen from a representation of the QRS signal that is to be detected. In other words, for a QRS detector the plot of the matched filter coefficients would look like a QRS complex. Rather than being frequency selective, a matched filter is sensitive to a specific shape. An example is now described.

FIG. 8 is a diagram 800 of coefficient values for a kernel of a matched filter for detecting a QRS complex of a sample patient according to embodiments. In diagram 800, the horizontal axis shows number of samples, while the vertical axis shows relative amplitude. The kernel of diagram 800 has been derived from a patient's ECG signal.

Figure 9:
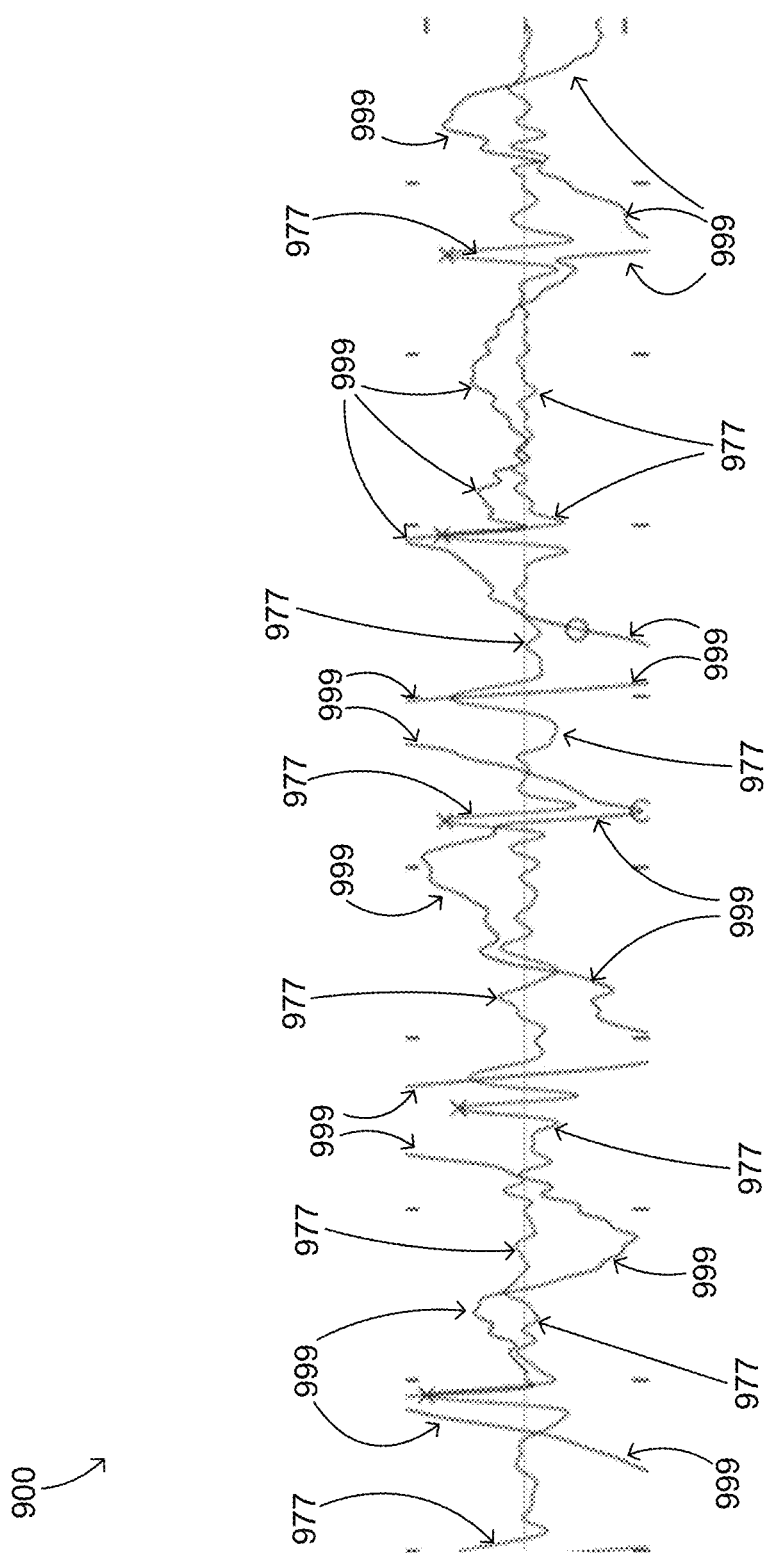
FIG. 9 is a time diagram of a sample ECG signal superimposed with an ECG signal that has been filtered according to embodiments by using the equation of FIG. 7.

Matched filtering according to embodiments improves ECG detection. An example of the improvement is seen in FIG. 9, which shows a time diagram 900 of a sample ECG signal 999 superimposed with an ECG signal 977 that has been match-filtered according to embodiments by using the equation of FIG. 7. Multiple segments are pointed in each, as they are plotted overlapping to best show their contrast. It will be seen that match-filtered ECG signal 977 permits detection of a lot more QRS complexes. In fact, "x"s are shown where detection has happened, all of which are true positive detections.

Matched filters for detecting QRS are suitable for a WCD, while possibly less in other applications. Indeed, a traditional ECG monitor may not be connected to a patient for a long enough time to form a kernel. Moreover, most ECG monitors do not have to work in the presence of extreme noise, such as seen above. Most monitors use adhesive electrodes and, if the ECG signal is too noisy, then better skin preparation is probably the best remedy. On the contrary, extreme noise can be tolerated even with using dry electrodes of a WCD system, which can be very noisy due to friction, and operation would not stop notwithstanding any and all artifacts. Additionally, a matched filter can be most appropriate for segment-based ECG processing; if, instead continuous processing is desired, an adaptive filter may be more appropriate. Also, most ECG monitors need to compute a heart rate in a way that responds reasonably quickly to changes. Segment-based processing may add delays, which are usually undesirable.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

FIG. 10 shows a flowchart 1000 for describing methods according to embodiments. According to an operation 1010, an ECG signal of the patient may be rendered, for example as described above.

According to another operation 1020, ECG data may be received, for example by a processor or a detector. The ECG data can be derived from the rendered ECG signal, with or without taking a time derivative of the rendered ECG signal.

According to another operation 1030, the received ECG data may be filtered with a matched filter. The matched filter may use coefficient values associated with a baseline QRS complex. If a time derivative of the rendered ECG signal has been taken, the coefficient values may represent a time derivative of the baseline QRS complex, instead of a QRS complex.

According to another operation 1060, QRS complexes may be detect in the ECG data. Detection may be by the filtering of operation 1030.

According to another operation 1070, a heart rate may be computed from the QRS complexes detected at operation 1060. For example, there may be averaging of how many QRS detected peaks occurred within a certain time. Or, time moments that successive detected peaks occur can be thought of as a period, which would be an inverse of a heart rate.

According to another operation 1080, it can be determine whether or not a shock criterion is met. The determination may be made from the computed heart rate. If the answer is no, then execution may return to another operation, for example operation 1010.

If the answer is yes then according to another operation 1090, the discharge circuit can be controlled to discharge the stored electrical charge through the patient while the support structure is worn by the patient. The purpose would be to deliver a therapeutic shock to the patient.

As mentioned above, in some embodiments a kernel can be stored in memory 238, and even become updated. So, the electrodes can be further configured to render previously a previous ECG signal of the patient, while the patient was previously wearing the support structure. In such embodiments, the processor can be further configured to register previous ECG data that were derived from the rendered previous ECG signal, and the coefficient values of the matched filter can be derived from the registered previous ECG data.

FIG. 11A shows a sample equation 1100A for computing outputs for a filter. For example, equation 1100A can be used by action block 631 when the filter is a matched difference filter.

Equation 1100A is for a matched difference filter according to embodiments, which is different from a matched filter. In equation 1100A, f(m) are the data values of the ECG signal, which can be as in FIG. 3. Moreover, in equation 1100A, g( ) can be the coefficient values that define the kernel of a convolution, and can be chosen from a representation of the QRS signal that is to be detected. In other words, in equation 1100A, g( ) can be a function having coefficient values associated with a baseline QRS complex, as also described for g( ) in equation 700.

Unlike with convolution, in Equation 1100A, Matched Difference Term MDT is subtracted from one. The MDT can itself be a function, and use a first function F[ ] of the values f(m), and a second function G[ ] of coefficient values g(m). The MDT can be a function of a difference of first function F[ ] and second function G[ ].

A convolution filter may multiply the f and g values. As such, outputs of a convolution filter can be proportional to the amplitude of the input signal. In other words, a larger input produces a larger output. Artifacts may pass through a convolution filter, if they are big enough, even if they don't match the filter kernel.

A matched difference filter can be implemented in a number of ways according to embodiments, often by choosing the MDT judiciously. In embodiments, the MDT is chosen such that the matched difference filter may detect complexes that are similar in shape and amplitude to the kernel g( ) This can be accomplished by having the MDT go to zero due to the aforementioned difference of F and G, which will make the output equal 1. At the same time, the matched difference filter can be made to reject artifacts that are transient signals of large amplitude by having the whole MDT term go to 1, which will make filter output go to zero. In addition, the matched difference filter can be used jointly with a matched filter, and so on.

Accordingly, the MDT may be implemented in a number of ways. One sample such way is now described.

FIG. 11B shows a particular sample equation 1100B that is a special case of equation 1100A, according to embodiments. The MDT term is a fraction. In this implementation, F[f(m)]=f(m), G[g(m)]=g(m), and the difference is in the numerator of the fraction, squared. The denominator takes care of the rest.

One skilled in the art will realize that equation 1100A can be implemented in additional ways. For example, an equation can be created that is similar to equation 1100B, where the absolute value of numerator is taken rather than squaring the numerator. Also, the numerator could be raised to a higher power, or the absolute value of the numerator could be raised to a higher power. In these situations the exponents in the denominator can be adjusted so that the fraction goes to one for large transients.

FIG. 12 shows a flowchart 1200 for describing methods according to embodiments. An operation 1210 can be performed as operation 1010. In addition, an operation 1220 can be performed as operation 1020, where further the ECG data have values f(m). Again, the ECG data can be derived from the rendered ECG signal, with or without taking a time derivative of the rendered ECG signal.

According to another operation 1230, there can be computed, from the values f(m), outputs for multiple values of a positive integer n according to equation 1100A in FIG. 11A of this document. In this computation, as also mentioned above, MDT may be a matched difference term that is a function of a difference of a first function F[ ] of the values f(m) and of a second function G[ ] of coefficient values g(m) that are associated with a baseline QRS complex. Again, if a time derivative of the rendered ECG signal has been taken, the coefficient values may represent a time derivative of the baseline QRS complex, instead of a QRS complex.

According to another operation 1260, QRS complexes can be detected from aspects of the outputs computed by operation 1230. Operations 1270, 1280 and 1290 can be performed as operations 1070, 1080 and 1090 respectively.

Again, and as mentioned above, in some embodiments a kernel can be stored in memory 238, and even become updated. So, the electrodes can be further configured to render previously a previous ECG signal of the patient, while the patient was previously wearing the support structure. In such embodiments, the processor can be further configured to register previous ECG data that were derived from the rendered previous ECG signal, and the coefficient values of g(m) in equation 1100 can be derived from the registered previous ECG data.

One way of detecting QRS peaks in the prior art may occasionally miss some QRS peaks. An example is now described.

Figure 13:
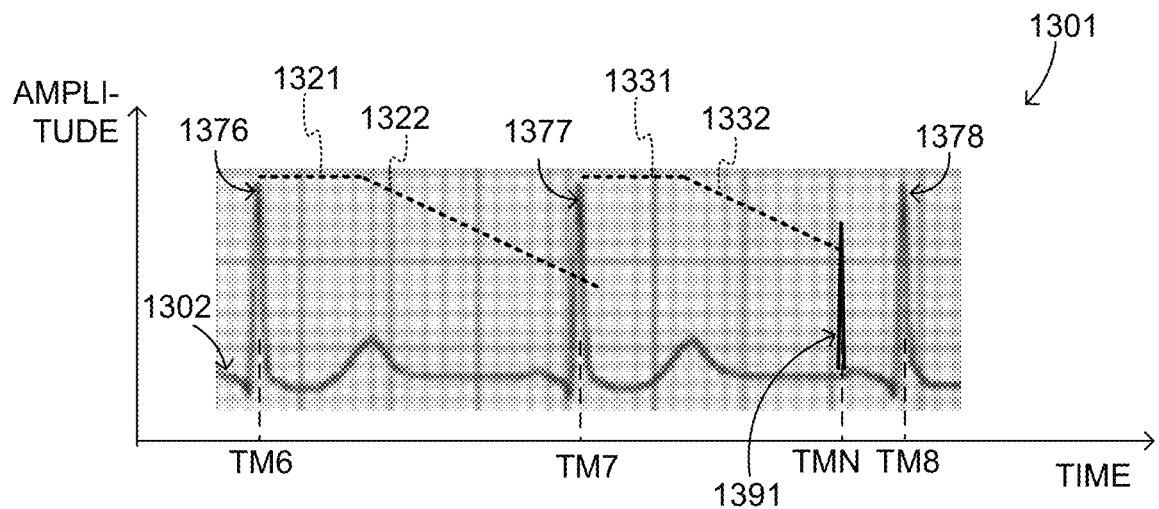
FIG. 13 is a time diagram for describing a QRS detection technique in the prior art.

FIG. 13 is a time diagram 1301 for describing a QRS detection technique in the prior art. Diagram 1301 plots amplitude against time. Diagram 1301 shows a QRS signal 1302, which exhibits QRS peaks 1376, 1377, 1378 at least at time moments TM6, TM7 and TM8, which occur at regular intervals in this example.

In particular, the prior art technique is to define a threshold line that declines from each detected QRS peak, and use the threshold line to detect the next peak. So, at time moment TM6, a threshold line segment 1321 has the same amplitude as the QRS peak detected then, and remains at that value for a refractory period. Then a threshold line segment 1322 declines in value, until another QRS peak 1377 is detected at TM7. Then the threshold includes similarly defined line segments 1331, 1332. Ordinarily the latter might detect the next QRS peak 1378 at TM8. A challenge, however, is that this detection technique is more sensitive to noise occurring immediately before a QRS complex. In this example, a noise spike 1391 at TMN may be instead detected as a peak of a QRS complex.

In some embodiments, QRS detection operations are performed by searching the ECG data backward and forward. That, while a time derivative may or may not have been taken as per the above. And thresholds can be set by looking backward and forward, where a detected QRS complex may be confirmed both ways. Examples are now described.

Figure 14:
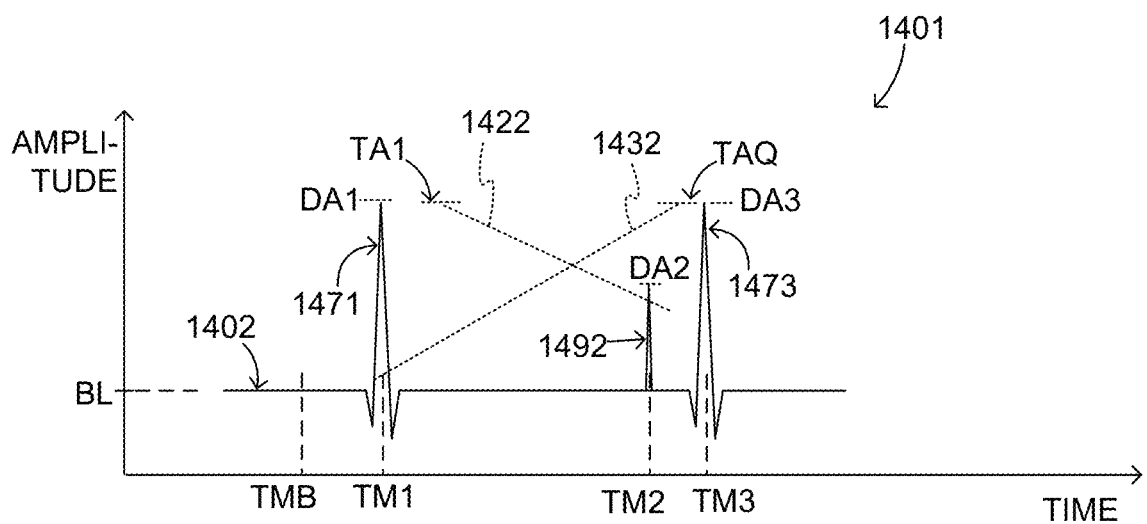
FIG. 14 is a time diagram for describing QRS detection according to embodiments.

FIG. 14 is a time diagram 1401 for describing QRS detection according to embodiments. Diagram 1401 plots amplitude against time. Diagram 1401 shows a QRS signal 1402, which exhibits QRS peaks 1471, 1473 at time moments TM1, TM3, and a noise spike 1492 at time T2, all with respect to a baseline amplitude BL. Noise spike 1492 should be rejected. It should be noted that a technique according to embodiments may tentatively identify noise spike 1492 as a peak, and may reject it later by using a forward threshold time function (FTTF) 1422 from peak 1471 plus a backward threshold time function (BTTF) from peak 1473. Of course, this process may have been used to eliminate also other noise spikes between peaks 1471 and 1473. Plus, peaks 1471, 1473 may become similarly challenged by their neighboring peaks, and so on. Such a method is now described.

Figure 15:
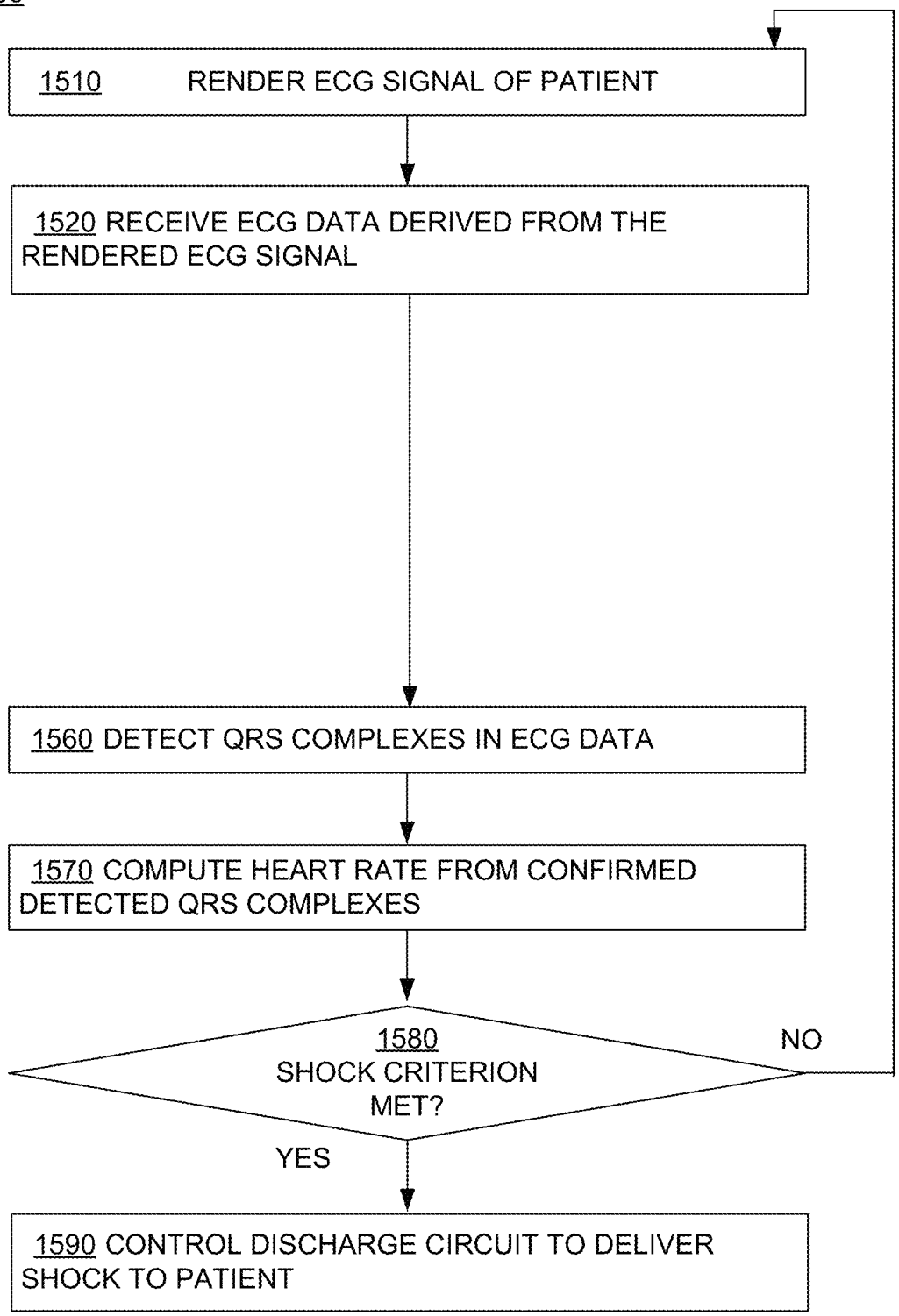
FIG. 15 is a flowchart for illustrating methods according to embodiments.

FIG. 15 shows a flowchart 1500 for describing methods according to embodiments. Operations 1510, 1520 can be performed as described for operations 1010, 1020. Again, the ECG data can be derived from the rendered ECG signal, with or without taking a time derivative of the rendered ECG signal. According to another operation 1560, QRS complexes can be detected. Such operations are described later in more detail. Operation 1570 can be performed similarly to what was described for operation 1070 adapted, of course, for confirmed peaks. Operations 1580 and 1590 can be performed similarly to what was described for operations 1080 and 1090 respectively.

For performing operation 1560, QRS complexes can be detected as per the above. Or, peaks in the ECG signal may be detected, and treated as if they are QRS complexes. In some embodiments, these peaks may be first confirmed as detected QRS complexes.

Figure 16:
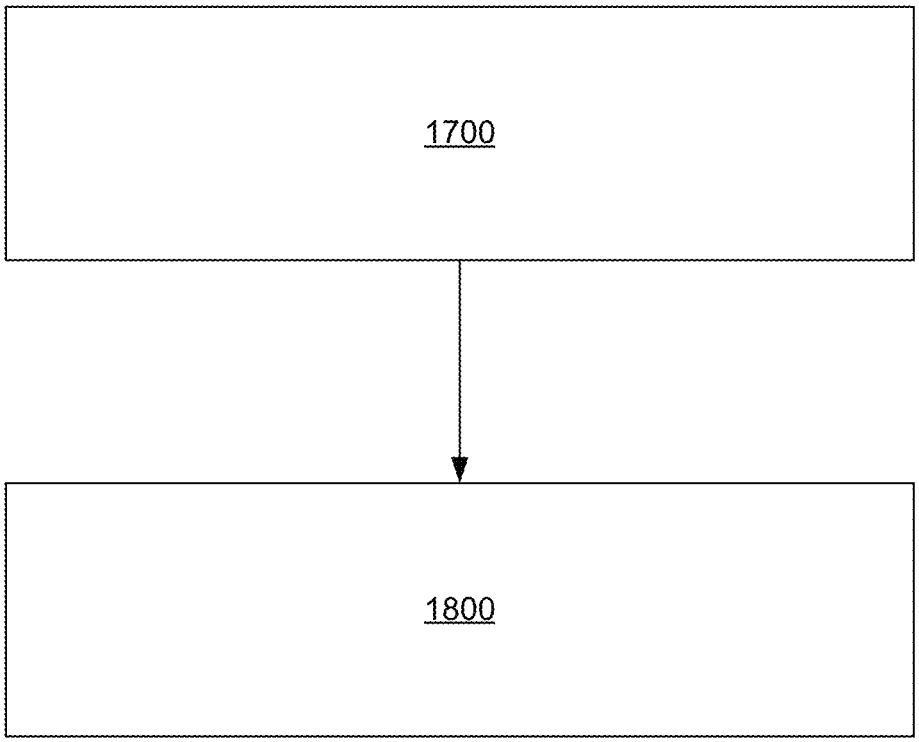
FIG. 16 is an overarching flowchart for illustrating methods according to embodiments in terms of two component flowcharts.

FIG. 16 shows an overarching flowchart 1660 for describing methods according to embodiments for performing operation 1560. Flowchart 1660 includes operations 1700 and then operations 1800, each of which is described in a component flowchart below.

Figure 17:
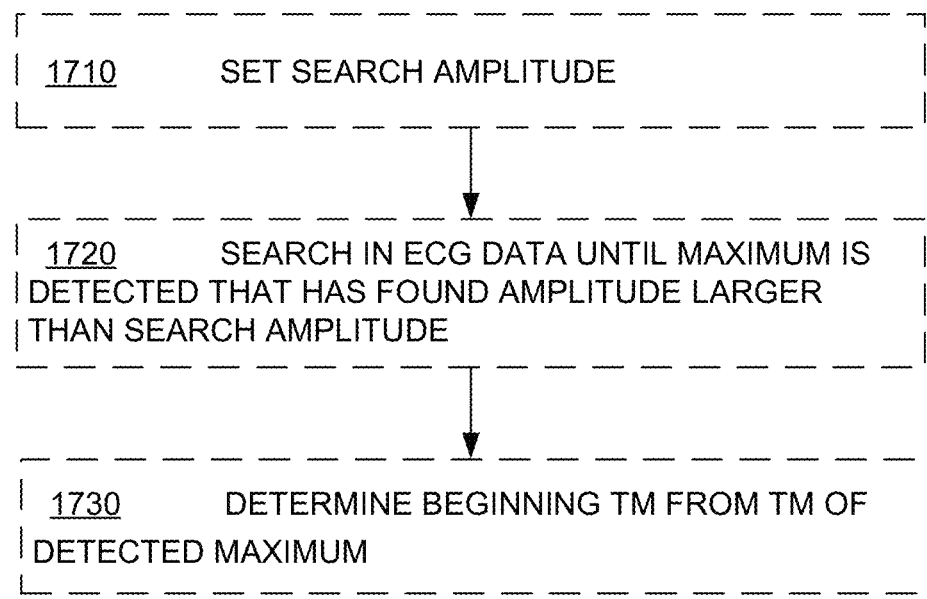
FIG. 17 is a sample component flowchart according to embodiments, which may be used in the overarching flowchart of FIG. 16.

FIG. 17 is a sample component flowchart for describing optional operations 1700 according to embodiments. According to an operation 1710, a search amplitude may be set, for detecting peaks.

According to another operation 1720, there may be searching in the ECG data until a maximum is detected that has a found amplitude larger than the search amplitude.

According to another, optional operation 1730, a beginning time moment (TM) may be determined from when a TM of the detected maximum occurs.

Figure 18:
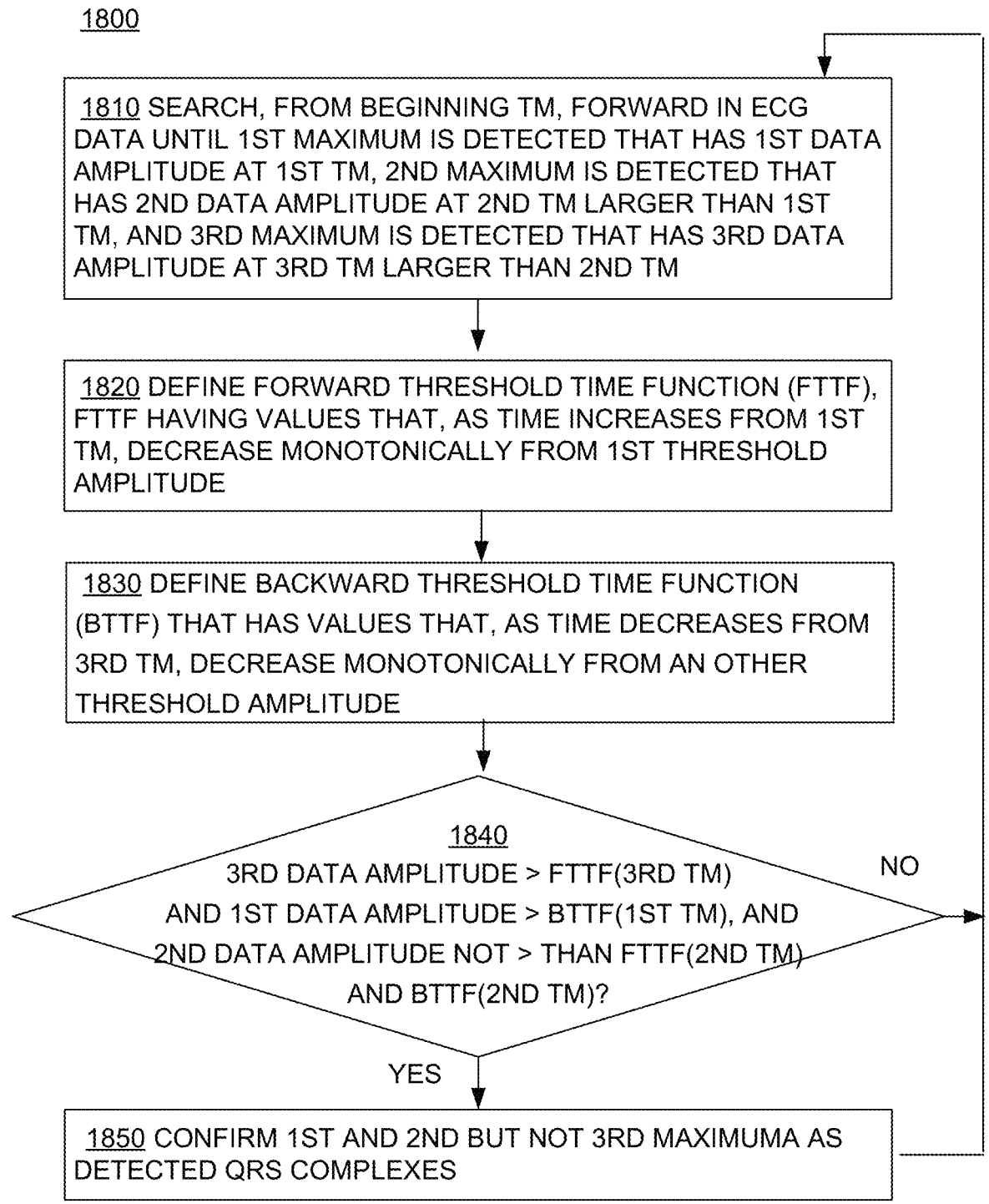
FIG. 18 is a sample component flowchart according to embodiments, which may be used in the overarching flowchart of FIG. 16.

FIG. 18 is a sample component flowchart for describing operations 1800 according to embodiments.

According to an operation 1810, there may be searching, from a beginning time moment (TM), forward in the ECG data until a first maximum is detected that has a first data amplitude at a first TM, a second maximum is detected that has a second data amplitude at a second TM larger than the first TM, and a third maximum is detected that has a third data amplitude at a third TM larger than the second TM. The beginning TM may be either random, or the beginning of an interval, or found in another way, for example as in operation 1730.

Applying operation 1810 to the example of FIG. 14, the beginning TM may be TMB. The first maximum can be peak 1471 that has a data amplitude DA1 at TM1, the second maximum can be peak 1492 that has a second data amplitude DA2 at TM2 occurring later than TM1, and the third maximum can be peak 1473 that has a data amplitude DA3 at TM3.

According to another operation 1820, a forward threshold time function (FTTF), may be defined. The FTTF is a time function, so it can be written as FTTF(time moment). The FTTF may have values that, as time increases from the first TM, decrease sometimes from a first threshold amplitude.

Applying operation 1820 to the example of FIG. 14, the FTTF may have values along line 1422, which decrease sometimes from a first threshold amplitude TA1 as time increases from the TM1. The first threshold amplitude TA1 can be determined from the first data amplitude DA1; in fact, the first threshold amplitude TA1 may equal the first data amplitude DA1.

According to another operation 1830, a backward threshold time function (BTTF) may be defined. The BTTF may have values that, as time decreases from the third TM, decrease sometimes from an other threshold amplitude.

Applying operation 1830 to the example of FIG. 14, the BTTF may have values along line 1432, which decrease sometimes from an other threshold amplitude TAQ as time decreases from TM3. The other threshold amplitude TAQ may be determined from the third data amplitude DA3; in fact, the other threshold amplitude TAQ may equal the third data amplitude DA3.

Either one or both of the FTTF and the BTTF may be linear, exponential, step-wise, and so on. They may even decline monotonically. In some embodiments, either the FTTF or the BTTF or both are declining exponential functions.

According to another operation 1840, it can be determined whether the first and the third maxima confirm each other while disconfirming the second maximum. In particular, it can be determined whether: (a) the third data amplitude is larger than a value of the FTTF at the third TM, (b) the first data amplitude is larger than a value of the BTTF at the first TM, and (c) the second data amplitude is not larger than both the FTTF at the second TM or the BTTF at the second TM.

Applying operation 1840 to the example of FIG. 14, it can be determined whether (a) DA3 is larger than FTTF(TM3) (here, YES), (b) DA1 is larger than BTTF(TM1) (here, YES), and (c) DA2 is not larger than both FTTF(TM2) or BTTF(TM2) (here, YES).

If, at operation 1840 the answer is no, then execution may return to another operation, such as operation 1810. If the answer is yes then, according to another operation 1850, the first and the third but not the second maxima can be confirmed as detected QRS complexes.

In embodiments, processor 230 may detect peaks in the ECG signal according to a variable threshold time function (TTF). The TTF may adjust for local amplitude variations of the ECG signal. Examples are now described.

Figure 19:
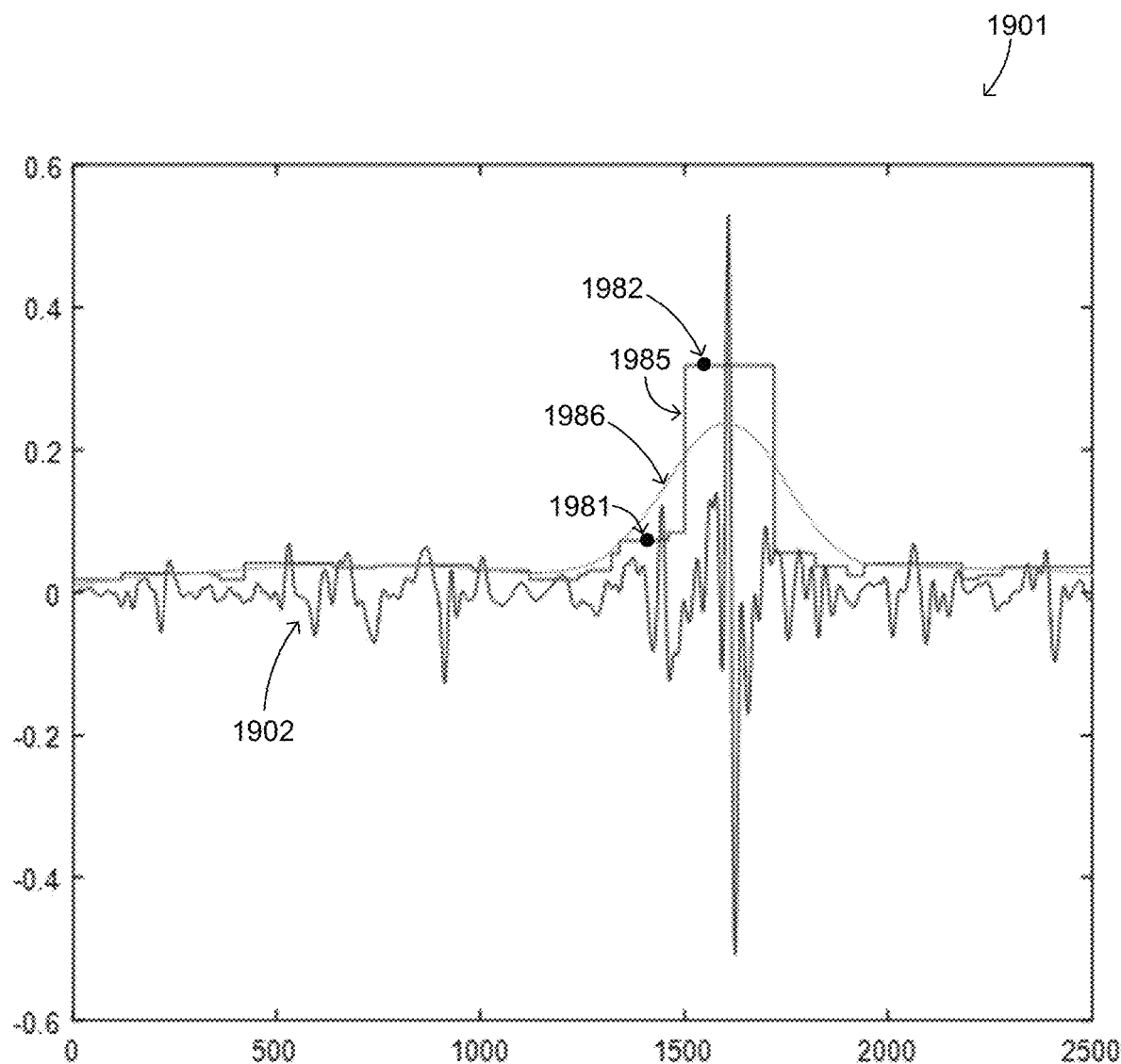
FIG. 19 is a time diagram of sample ECG data, along with a superimposed threshold functions for explaining how detection of peaks in the ECG signal may be performed according to embodiments.

FIG. 19 is a time diagram 1901 of sample ECG data 1902. A time derivative may or may not have been taken, as per the above.

In some embodiments, a variable threshold time function (TTF) is defined based on ECG data 1902. For example, one embodiment is a TTF 1985, which moves stepwise. In embodiments, the ECG data is arranged in time segments, and the TTF has respective values for the time segments that are derived from the ECG data in the respective time segments. Thus, in some embodiments, the TTF can have at least initially a single value for the entire segment.

Moreover, these values of the TTF can be defined looking backward to previous values plus forward to future values. The latter is possible because data is stored. As such, it is possible that the TTF has, at a first one of the time segments, a value 1981 that is defined from at least the value of the ECG data at a second one of the time segments that occurs after the first segment. That second time segment has, in this example, a value 1982.

In some embodiments, processor 230 is further configured to identify a time segment of the ECG data, and set an initial threshold value depending on a value of the ECG data within the identified time segment. The threshold may be set to a fraction (e.g. 80%) of the maximum value of the ECG signal within the time interval. Then the processor may define the TTF based also on the initial threshold value. For instance, as seen in the example of FIG. 19, TTF 1985 has an initial threshold value defined, from the very beginning of the time plot, by values of the ECG data 1902.

In some embodiments, the TTF is defined based on ECG data 1902, and also by low-pass filtering ECG data 1902. Filtering may be performed in both the forward and reverse directions which maintains the time alignment between the threshold and the ECG. For example, one embodiment is a TTF 1986, which has been filtered in the forward and reverse directions and moves more smoothly than TTF 1985.

Detection of a peak may be defined as to time moments (TMs) when the ECG data has values larger than the TTF. If two peaks are too close to each other, one of them may be treated as spurious and, if so, confirmed rejected. For example, a certain one of the peaks may have a certain amplitude and occur at a certain time moment (TM), and a spurious one of the peaks may have a spurious amplitude and occur at a spurious TM that is within an error time interval of the first TM. The error interval may be short, e.g. 0.2 sec. In such instances, the heart rate may be computed by not including the spurious peak responsive to the spurious amplitude being less than the certain amplitude.

FIG. 20 shows a flowchart 2000 for describing methods according to embodiments. Operations 2010, 2020 can be performed as described for operations 1010, 1020. Again, the ECG data can be derived from the rendered ECG signal, with or without taking a time derivative of the rendered ECG signal.

According to another operation 2060, peaks can be detected in the ECG data. For example, according to a sub-operation 2061, the ECG data may be arranged in time segments. Then, according to a sub-operation 2062, a variable threshold time function (TTF) can be defined for time moments (TMs) of the ECG data.

As seen above, in some embodiments, the threshold time function (TTF) has respective values for the time segments derived from the ECG data in the respective time segments. In fact, the TTF may have, at a first one of these time segments, a value that is defined from at least the value of the ECG data at a second one of these time segments that occurs after the first segment. The value for the TTF for the first time segment can also be defined from a value of the ECG data at another time segment that occurs before the first time segment.

Moreover, according to a subsequent sub-operation 2064, time moments (TMs) may be detected as peaks when the ECG data has values larger than the TTF. Some examples were seen earlier, with reference to FIG. 19. In fact, it will be appreciated that these sub-operations are also another way for performing peak detection operations such as operation 1560 of FIG. 15, operation 2260 of FIG. 22, and so on, as adapted of course for the particular data that is being used. Again, the TTF may be defined based values of the ECG data, and also its initial threshold value may be so defined. And the TTF may be low-pass filtered, etc.

Operation 2070 can be performed similarly to what was described for operation 1070, as adapted, of course, to the exact data being used. Operations 2080 and 2090 can be performed similarly to what was described for operations 1080 and 1090 respectively.

In some embodiments, upon searching for peaks in the ECG signal, processor 230 may detect peaks of both polarities, positive and negative. An example is now described.

Figure 21A:
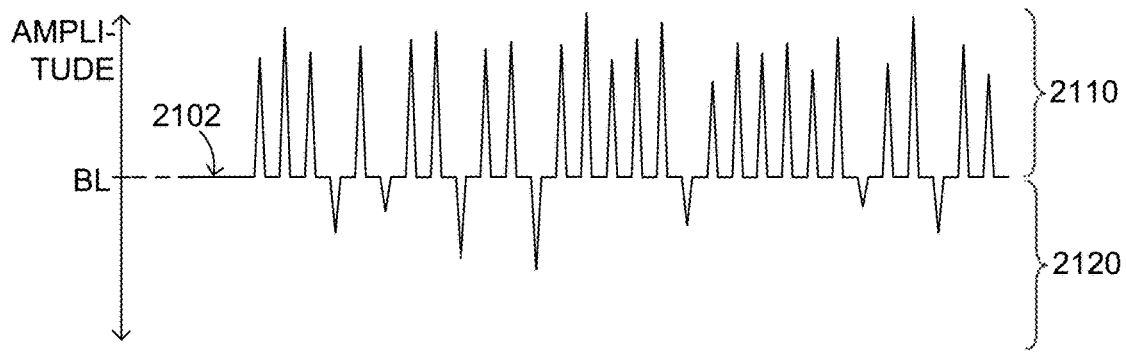
FIGS. 21A-21C show a series of time diagrams of sample ECG data, or waveforms, in successive stages of processing according to embodiments.

FIG. 21A shows a time diagram of sample ECG data 2102, which may have been derived from the rendered ECG signal according to some embodiments. In ECG data 2102, positive peaks 2110 and negative peaks 2120 may be detected. In other words, there are peaks of both polarities, positive and negative. The peaks are shown as being above or below a single baseline level BL, which is shown here for simplicity of explanation. In fact, it is not necessary there be a single baseline level.

In such embodiments, processor 230 may then compute a selection statistic for determining which of the polarities to prefer. The selection statistic may be chosen to point to which group of peaks to prefer. For example, the peaks of larger amplitude may be preferred. In such cases, the selection statistic may include a first statistic of amplitudes of the positive peaks, and a second statistic of amplitudes of the negative peaks. The first statistic may be, for example, median amplitude, average amplitude, and so on. Then it can be determined to prefer the positive peaks over the negative peaks if the first statistic is larger than the second statistic, and vice versa.

Figure 21B:
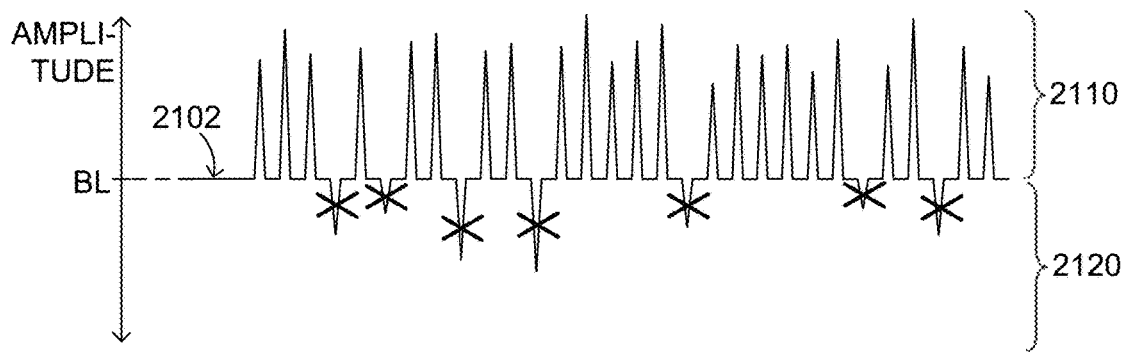

In this example, positive peaks 2110 of the positive polarity are preferred. Processor 230 may then reject peaks of the polarity that is not the preferred polarity. As seen in FIG. 21B, ECG data 2102 is repeated, where further all negative peaks 2120 of the non-preferred negative polarity have been crossed out, to indicate that they will be rejected from the computation of the heart rate. In this case, all the peaks of the non-preferred polarity are shown as rejected, as is preferred but not necessary for embodiments.

Figure 21C:
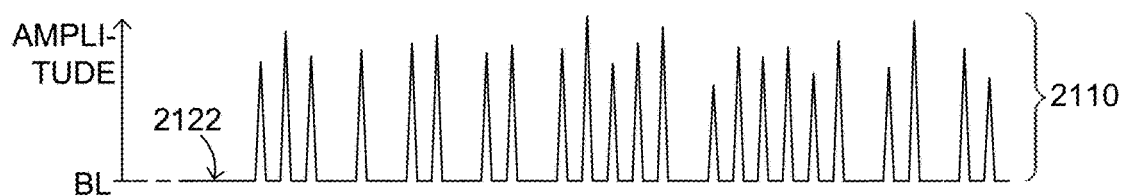

FIG. 21C shows ECG data 2122, which have been derived from ECG data 2102 after the non-preferred negative peaks 2120 have been removed, as per FIG. 21B. Processor 230 may then compute a heart rate from ECG data 2122, in other words by rejecting peaks of the polarity that is not preferred. The heart rate computation may thus be more accurate, for example if it succeeds in removing ectopic beats such as premature ventricular contractions.

FIG. 22 shows a flowchart 2200 for describing methods according to embodiments. Operations 2210, 2220 can be performed as described for operations 1010, 1020. Again, the ECG data can be derived from the rendered ECG signal, with or without taking a time derivative of the rendered ECG signal.

According to another operation 2260, peaks may be detected in the ECG signal. Some of the peaks may be positive while some of the peaks may be negative, as was seen in FIG. 21A. And, again, if two peaks are too close to each other, one of them can be suspected as spurious and, if confirmed, be rejected.

According to another operation 2263, a selection statistic of at least some of the positive peaks or at least some of the negative peaks may be computed. And, according to another operation 2265, it may be determined, according to the selection statistic, whether to prefer the positive peaks over the negative peaks or vice versa.

According to another operation 2270, the heart rate can be computed according to the detected peaks, by not including at least some of the peaks that are not preferred. In some embodiments, the heart rate is computed from the detected peaks by not including any of the peaks that are not preferred.

Operations 2280 and 2290 can be performed similarly to what was described for operations 1080 and 1090 respectively.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Anything written in the background section of this document is not, and should not be taken as, an acknowledgement or any form of suggestion that such is already known in the art, except where it is expressly pointed out. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A wearable monitoring device, comprising:
a support structure configured to be worn by a patient;
electrodes configured to obtain an electrocardiogram (ECG) signal of the patient while the patient is wearing the support structure, wherein the electrodes are dry electrodes; and
a processor configured to:
process the ECG signal to detect a QRS complex in the ECG signal using an adaptive matched filter, wherein the adaptive matched filter is configured to detect the QRS complex in the ECG signal having noise caused by friction between the patient and the dry electrodes;
assess similarity between two or more QRS complexes in the ECG signal, and to provide an organization value based on the assessed similarity; and
compute a heart rate of the patient based at least in part on the detected QRS complex and the organization value.

2. The wearable monitoring device of claim 1, further comprising:
a heart rate monitor to obtain the heart rate of the patient;
wherein the processor is configured to assess agreement between the computed heart rate and the heart rate obtained with the heart rate monitor, and to provide an agreement value based on the assessed agreement.

3. The wearable monitoring device of claim 2, wherein the processor is configured to update a kernel of the adaptive matched filter when the agreement value is high or when the organization value is high.

4. The wearable monitoring device of claim 2, wherein the processor is configured to update a kernel of the adaptive matched filter when both the agreement value and the organization value are high.

5. The wearable monitoring device of claim 1, wherein the ECG signal is processed by the processor without taking a time derivative of the ECG signal.

6. The wearable monitoring device of claim 1, wherein the processor is configured to take a time derivative of the ECG signal to process the ECG signal.

7. The wearable monitoring device of claim 1, wherein the ECG signal passes through a series connected capacitor prior to being processed by the processor.

8. The wearable monitoring device of claim 1, wherein the processor is configured to continuously process the ECG signal using the adaptive matched filter.

9. The wearable monitoring device of claim 1, wherein the processor is configured to process segments of the ECG signal using the adaptive matched filter.

10. The wearable monitoring device of claim 1, further comprising:
an energy storage module configured to store an electrical charge; and
a discharge circuit coupled to the energy storage module;
wherein the processor is further configured to:
determine based at least in part on the computed heart rate whether a shock criterion is met; and
responsive to the shock criterion being met, control the discharge circuit to discharge at least a portion of the stored electrical charge through the patient while the support structure is worn by the patient to deliver a shock to the patient.

11. A wearable monitoring device, comprising:
a support structure configured to be worn by a patient;
electrodes configured to obtain an electrocardiogram (ECG) signal of the patient while the patient is wearing the support structure, wherein the electrodes are dry electrodes; and
a processor configured to:
detect a QRS complex in the ECG signal by processing the ECG signal using a first filter and processing the ECG signal using a second filter, and detecting the QRS complex when both the first filter and the second filter output the QRS complex, wherein at least one of the first filter or the second filter is configured to detect the QRS complex in the ECG signal having noise caused by friction between the patient and the dry electrodes, and wherein the first filter is a matched convolution filter and the second filter is a matched difference filter; and
compute a heart rate of the patient based at least in part on the detected QRS complex.

12. The wearable monitoring device of claim 11, wherein one of the first filter or the second filter is an adaptive matched filter.

13. The wearable monitoring device of claim 11, wherein the processor is configured to process the ECG signal in segments.

14. The wearable monitoring device of claim 13, wherein a successive segment at least partially overlaps a previous segment.

15. The wearable monitoring device of claim 11, wherein the processor is configured to continuously process the ECG signal.

16. The wearable monitoring device of claim 11, wherein the processor comprises a digital signal processor (DSP), and the first filter and the second filter comprise digital filters.

17. The wearable monitoring device of claim 11, further comprising:
an energy storage module configured to store an electrical charge;
a discharge circuit coupled to the energy storage module;
wherein the processor is further configured to:
determine based at least in part on the computed heart rate whether a shock criterion is met; and
responsive to the shock criterion being met, control the discharge circuit to discharge at least a portion of the stored electrical charge through the patient while the support structure is worn by the patient to deliver a shock to the patient.

18. A wearable monitoring device, comprising:
a support structure configured to be worn by a patient;
electrodes configured to obtain an electrocardiogram (ECG) signal of the patient while the patient is wearing the support structure; and
a processor configured to:
process the ECG signal to detect a QRS complex in the ECG signal using an adaptive matched filter;
assess similarity between two or more QRS complexes in the ECG signal, and to provide an organization value based on the assessed similarity; and
compute a heart rate of the patient based at least in part on the detected QRS complex and the organization value.

19. The wearable monitoring device of claim 18, further comprising:
a heart rate monitor to obtain the heart rate of the patient;
wherein the processor is configured to assess agreement between the computed heart rate and the heart rate obtained with the heart rate monitor, and to provide an agreement value based on the assessed agreement, and to update a kernel of the adaptive matched filter when the agreement value is high.

20. The wearable monitoring device of claim 18, further comprising:
an energy storage module configured to store an electrical charge; and
a discharge circuit coupled to the energy storage module;
wherein the processor is further configured to:
determine based at least in part on the computed heart rate whether a shock criterion is met; and
responsive to the shock criterion being met, control the discharge circuit to discharge at least a portion of the stored electrical charge through the patient while the support structure is worn by the patient to deliver a shock to the patient.

* * * * *